(12) United States Patent
Honda et al.

(10) Patent No.: US 10,228,332 B2
(45) Date of Patent: Mar. 12, 2019

(54) DEFECT INSPECTION DEVICE AND DEFECT INSPECTION METHOD

(71) Applicant: Hitachi High-Technologies Corporation, Minato-ku, Tokyo (JP)

(72) Inventors: Toshifumi Honda, Tokyo (JP); Yuta Urano, Tokyo (JP); Shunichi Matsumoto, Tokyo (JP); Taketo Ueno, Tokyo (JP); Yuko Otani, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 3 days.

(21) Appl. No.: 15/127,686

(22) PCT Filed: Jan. 22, 2015

(86) PCT No.: PCT/JP2015/051720
§ 371 (c)(1),
(2) Date: Sep. 20, 2016

(87) PCT Pub. No.: WO2015/151557
PCT Pub. Date: Oct. 8, 2015

(65) Prior Publication Data
US 2017/0146463 A1    May 25, 2017

(30) Foreign Application Priority Data

Mar. 31, 2014  (JP) .................................. 2014-074098

(51) Int. Cl.
*G01N 21/956* (2006.01)
*G01N 21/95* (2006.01)
(Continued)

(52) U.S. Cl.
CPC ....... *G01N 21/956* (2013.01); *G01N 21/4738* (2013.01); *G01N 21/9501* (2013.01);
(Continued)

(58) Field of Classification Search
CPC .................................................... G01N 21/956
(Continued)

(56) References Cited

U.S. PATENT DOCUMENTS 4,672,196 A * 6/1987 Canino ................ G01B 11/065
250/225
5,736,735 A   4/1998 Hagiwara
(Continued)

FOREIGN PATENT DOCUMENTS

JP    9-61366 A    3/1997
JP    9-138364 A   5/1997
(Continued)

OTHER PUBLICATIONS

International Search Report (PCT/ISA/210) issued in PCT Application No. PCT/JP2015/051720 dated Apr. 21, 2015, with English translation (four (4) pages).

*Primary Examiner* — Tarifur Chowdhury
*Assistant Examiner* — Omar Nixon
(74) *Attorney, Agent, or Firm* — Crowell & Moring LLP

(57) ABSTRACT

A defect inspection method includes irradiating a sample with laser, condensing and detecting scattered light beams, processing signals that detectors have detected and extracting a defect on a sample surface, and outputting information on the extracted defect. Detection of the scattered light beams is performed by condensing the scattered light beams, adjusting polarization directions of the condensed scattered light beams, mutually separating the light beams depending on the polarization direction, and detecting the light beams by a plurality of detectors. Extraction of the defect is performed by processing output signals from the detectors by multiplying each detection signal by a gain, discriminating between a noise and the defect, and detecting the defect.

14 Claims, 14 Drawing Sheets

(51) Int. Cl.
*G01N 21/47* (2006.01)
*G01N 21/88* (2006.01)

(52) U.S. Cl.
CPC ........ *G01N 2021/4792* (2013.01); *G01N 2021/8848* (2013.01); *G01N 2201/121* (2013.01)

(58) Field of Classification Search
USPC ........................................................ 356/369
See application file for complete search history.

(56) References Cited

U.S. PATENT DOCUMENTS

| | | | | |
|---|---|---|---|---|
| 5,751,408 | A * | 5/1998 | Ohtomo | G01C 15/004 356/5.14 |
| 5,764,363 | A | 6/1998 | Ooki et al. | |
| 2003/0151811 | A1* | 8/2003 | Helbing | G02B 6/264 359/484.04 |
| 2003/0184744 | A1 | 10/2003 | Isozaki et al. | |
| 2004/0017761 | A1* | 1/2004 | Aoyama | G02B 5/3083 369/112.17 |
| 2004/0169859 | A1* | 9/2004 | Smith | G01N 21/1717 356/369 |
| 2004/0227898 | A1* | 11/2004 | Ma | H04N 9/3114 353/20 |
| 2005/0157295 | A1* | 7/2005 | Chegal | G01J 3/447 356/369 |
| 2007/0268807 | A1* | 11/2007 | Kimura | G11B 7/131 369/112.16 |
| 2008/0297783 | A1* | 12/2008 | Urano | G01N 21/9501 356/237.5 |
| 2010/0004875 | A1* | 1/2010 | Urano | G01N 21/4738 702/40 |
| 2010/0014075 | A1 | 1/2010 | Ueno et al. | |
| 2012/0019816 | A1 | 1/2012 | Shibata et al. | |
| 2012/0050693 | A1* | 3/2012 | Yanai | G03B 21/2013 353/31 |
| 2012/0061356 | A1* | 3/2012 | Fukumitsu | B23K 26/0057 219/121.61 |
| 2013/0215404 | A1* | 8/2013 | Den Boef | G01J 3/4412 355/44 |
| 2013/0321798 | A1 | 12/2013 | Urano et al. | |
| 2015/0168290 | A1* | 6/2015 | Shachaf | G02B 7/28 356/369 |

FOREIGN PATENT DOCUMENTS

| | | |
|---|---|---|
| JP | 2003-287504 A | 10/2003 |
| JP | 2010-25713 A | 2/2010 |
| JP | 2010-190722 A | 9/2010 |
| JP | 2012-98103 A | 5/2012 |

* cited by examiner

1501

15021
15022
15023
15024

1502

1503

1504

| | |
|---|---|
| 1906 ·······> | SAMPLE SURFACE POLARIZATION DIRECTION |
| 1907 <—> | PHASE ADVANCE AXIS DIRECTION |

| | |
|---|---|
| 2006 ·······> | DEFECT POLARIZATION DIRECTION |
| 2007 <—> | PHASE ADVANCE AXIS DIRECTION |

DEFECT INSPECTION DEVICE AND DEFECT INSPECTION METHOD

BACKGROUND

The present invention relates to defect inspection device and defect inspection method for inspecting a fine defect that is present on a surface of a sample, and deciding and outputting the position, the kind and, the size of the defect.

On manufacturing lines of a semiconductor substrate, a thin film substrate and so forth, inspections of the defects present on the surfaces of the semiconductor substrate, the thin film substrate and so forth are made in order to maintain and improve the yield of products. As an existing defect inspection technology, a technology described in, for example, Japanese Unexamined Patent Application Publication No. 2010-190722 is known.

In Japanese Unexamined Patent Application Publication No. 2010-190722, there is a description that "an optical detection path is polarization-diverged so as to arrange array-like spatial filters on at least one or more optical paths and to filter diffracted light and scattered light from a normal pattern".

SUMMARY

In the defect inspection used in a manufacturing process of a semiconductor and so forth, to detect the fine defect, to highly accurately measure the size of the detected defect, to inspect a sample nondestructively (for example, with no quality change of the sample), to obtain a substantially fixed inspection result in regard to, for example, the number of detected defects, the position of each defect, the size of each defect, the kind of each defect and so forth when the same sample has been inspected, to inspect many samples in a fixed period of time and so forth are demanded.

In the technology described in Japanese Unexamined Patent Application Publication No. 2010-190722, in particular, as for the fine defect of not more than, for example, about 20 nm in size, since scattered light generated from the fine defect is very weakened, becomes difficult to discriminate between the scattered light generated from the defect and background scattered light. When the fine defect is to be detected, it is possible to detect the scattered light from defect an a relatively high intensity of light in comparison with the light intensity of the background scattered light from the sample by obliquely making linearly polarized illumination incident upon a unit concerned as polarized illumination. Here, in general, polarization directions of the background scattered light from the sample and the scattered light from the defect are changed depending on an emission direction of the scattered light. That is, it is difficult to detect the scattered light from the defect as much as possible performing polarization divergence on the optical path.

In addition, although the spatial filter is effective when a background pattern has a specific cycle, when a spatial frequency that the background pattern has is widely distributed, there is such a drawback that a region to be light-shielded by the spatial filter is widened and the region so widened hinders detection of the scattered light from the defect.

That is, microminiaturization of the size of the defect induces relative reduction in strength of a defect signal with reflected light, scattered light and so forth from a surface of an inspection sample and makes detection of the defect difficult. Although there is an existing technology that copes with this drawback by performing polarized light detection, it is difficult for the abovementioned technology to separate the defect signal from background light scattered from the sample surface in principle.

The present invention has been made in view of the abovementioned circumstances and aims to provide a defect inspection device that makes it possible to surely detect the scattered light from the fine defect that would be mixed in the background scattered light from the sample by reducing the influence of the background scattered light and thereby highlighting the scattered light from the defect, and also aims to provide a defect inspection method using the abovementioned defect inspection device.

According to one embodiment of the present invention, there is provided a detect in method that includes adjusting a polarization state and an intensity distribution of laser that has been emitted from a light source unit, shaping the laser into light that is long in one direction and is short in a direction that is orthogonal to one direction, and irradiating a surface of a sample with the shaped laser light from a direction inclined relative to a normal direction of the surface of the sample, condensing scattered light beams generated from the sample that has been irradiated with the shaped laser light and detecting the condensed light beams by a plurality of detectors, processing signals obtained by detecting the scattered light beams by the plurality of detectors and extracting a defect on the surface of the sample, and outputting information on the extracted defect. Condensing the scattered light beams and detecting the condensed light beams by the plurality of detectors are performed by condensing the scattered light beams generated from the sample that has been irradiated with the laser by a condensing lens, adjusting a polarization direction of the scattered light beams that have been condensed by the condensing lens, mutually separating the scattered light beams of which the polarization directions have been adjusted depending on the polarization direction, and detecting the respective scattered light beams that have been mutually separated depending on the polarization direction. Processing the signals obtained by detecting the scattered light beams by the plurality of detectors and extracting the defect on the surface of the sample are performed by processing output signals that have been adjusted by respectively multiplying detection signals of the respective scattered light beams so separated depending on the polarization direction by gains and have been output from the plurality of detectors that have detected the scattered light beams, discriminating between a noise and a defect, and detecting the defect.

In addition, according to another embodiment of the present invention, there is provided a defect inspection device that includes a light source unit that emits laser, a laser irradiation unit that adjusts a polarization state and an intensity distribution of the laser that has been emitted from the light source unit, shapes the laser into light that is long in one direction and is short in a direction that is orthogonal to one direction, and irradiates a surface of a sample with the shaped laser light from a direction inclined relative to a normal direction of the surface of the sample, a scattered light detection unit that condenses and detects scattered light beams generated from the sample that has been irradiated with the laser by the laser irradiation unit, a defect signal processing unit that processes signals obtained by detecting the scattered light beams by a plurality of detectors of the scattered light detection unit and extracts a defect on the surfaces of the sample, and an output unit that outputs information on the defect that has been extracted by the defect signal processing unit. The scattered light detection unit includes a condensing lens that condenses the scattered light beams generated from the sample that has been irradiated with the laser, a polarization adjustment unit that adjusts polarization directions of the scattered light beams condensed by the condensing lens, a polarization separation unit that mutually separates the scattered light beams of which the polarization directions have been adjusted by the polarization adjustment unit depending on the polarization direction, and a plurality of detectors that detect the respective scattered light beams that have been separated depending on the polarization direction by the polarization separation unit. The defect signal processing unit includes a gain setting unit that sets gains for output signals from the plurality of detectors of the scattered light detection unit that have detected the scattered light beams, and a defect decision unit that processes the output signals that have been adjusted by the gains set by the gain setting unit and have been output from the plurality of detectors, discriminates between a noise and defect, and detects the defect.

According to the embodiments of the present invention, it is possible to provide the defect inspection device and the defect inspection method that make them possible to detect a fine defect, to highly accurately calculate the size of the detected defect, and to output a stable inspection result while scanning the entire surface of the sample in a short period of time and reducing heat damage imposed on the sample.

Subject matters, configurations and advantageous effects other than the above will become apparent from the following description on the embodiments.

DETAILED DESCRIPTION

In the following, embodiments of the present invention will be described by using the appended drawings.

First Embodiment

Figure 1A:
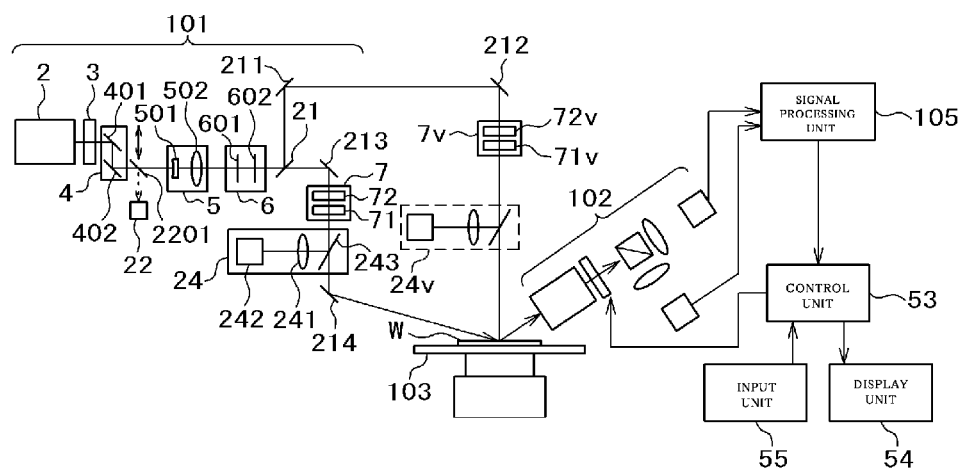
FIG. 1A is a block diagram illustrating one example of a whole schematic configuration of a defect inspection device according to a first embodiment of the present invention.

FIG. 1A is a block diagram illustrating one example of a schematic configuration of a defect inspection device according to the first embodiment of the present invention. The defect inspection according to the present embodiment includes an illumination unit 101, a detection unit 102, a stage 103 on which a sample W is freely placed, a signal processing unit 105, a control unit 53, a display unit 54, an input unit 55 and so forth. The illumination unit 101 appropriately includes a laser light source 2, an attenuator 3, an outgoing light adjustment unit 4, a beam expander 5, a polarization control unit 6, an illumination intensity distribution control unit 7 and so forth.

In the defect inspection device that includes the above-mentioned constitutional elements, a laser light beam that has been emitted from the laser light source 2 is adjusted by the attenuator 3 so as to have a desired beam intensity, is adjusted by the outgoing light adjustment unit 4 so as to have a desired beam position and a desired beam traveling direction, is adjusted by the beam expander 5 so as to have a desired beam diameter, is adjusted by the polarization control unit 6 so as to have a desired polarization state, is adjusted by the illumination intensity distribution control unit 7 so as to have a desired intensity distribution, and is radiated to an inspection object region of the sample W.

An incident angle of illumination light relative to a surface of the sample W is determined in accordance with positions and angles of reflection mirrors 401 and 401 of the outgoing light adjustment unit 4 that is arranged in an optical path of the illumination unit 101. The incident angle of the illumination light is set to an angle suited for detection of a fine defect.

Since the larger the incident angle of the illumination light is, that is, the smaller an elevation angle (an angle between the surface of the sample W and an optical axis of the illumination light) of the illumination light is, the more scattered light (called a haze) from micro-asperity on the sample surface that would become noise for scattered light from a fine foreign substance on the sample surface is weakened, it is suitable for detection of the fine defect to set the incident angle of the illumination light larger. Therefore, when the scattered light from the micro-asperity on the surface of the sample W hinders detection of the fine defect, the incident angle of the illumination light may be preferably set to at least about 75 degrees (the elevation angle of the illumination light may be set to not more than about 15 degrees).

On the other hand, in oblique incidence illumination, the smaller the incident angle of the illumination light is, the more an absolute amount of the scattered light from the fine foreign substance is increased. Therefore, when a shortage of an amount of light scattered from the defect hinders detection of the fine defect, the incident angle of the illumination light may be preferably set to at least about 60 degrees and not more than about 75 degrees (the elevation angle of the illumination light may be set to at least about 15 degrees and not more than about 30 degrees).

In addition, when oblique incidence illumination is performed, polarization is controlled by the polarization control unit 6 of the illumination unit 101 so as to use p-polarized light as polarized light for illumination and thereby the amount of the scattered light from the defect on the surface of the sample W is more increased than the amount obtained when other polarized light is used. In addition, when the scattered light from the micro-asperity on the surface of the sample W hinders detection of the fine defect, s-polarized light is used as the polarized light for illumination and thereby the amount of the scattered light from the micro-asperity on the surface of the sample W is more reduced than the amount obtained when other polarized light is used.

In addition, as illustrated in FIG. 1A, a mirror 21 is inserted into the optical path of the illumination unit 101 and other mirrors 211 and 212 are appropriately arranged as demanded. Thereby, an illumination optical path is changed and the surface of the sample W is irradiated with the illumination light from a substantially vertical direction (vertical illumination). At this time, an illumination intensity distribution on the sample surface is controlled by an illumination intensity distribution control unit 7v similarly to the illumination intensity distribution of the oblique incidence illumination. In order to obtain scattered light from a recessed defect (such as a polishing scratch, a crystal defect in a crystal material and so forth) on the surface of the sample W to the scattered light obtained in the oblique incidence illumination by inserting a beam splitter to the position where the mirror 21 is installed, the vertical illumination that the light is incident upon the surface of the sample W substantially vertically is suitable. Incidentally, an illumination intensity distribution monitor 24 illustrated in FIG. 1A will he described later.

In a state of leaving the mirror 21 put on standby at a position displaced from within the optical path of the illumination unit 101, the laser emitted from the laser light source 2 is reflected from a mirror 213, passes through the illumination intensity distribution control unit 7 and the illumination intensity distribution monitor 24, is then reflected from a mirror 214, is incident upon the surface of the sample W obliquely (a direction inclined relative to a normal direction of the surface of the sample W) and illuminates the surface of the sample W. Incidentally, when the sample W is to be irradiated with the illumination light, a mirror 243 of the illumination intensity distribution monitor 24 is withdrawn from the optical path of the illumination light.

As the laser light source 2, a light source of the type of oscillating ultraviolet or vacuum ultraviolet laser beams of a short wavelength (not more than about 355 nm in wavelength) as a wavelength that makes it difficult for light to penetrate into the sample W and emitting high-output light of at least about 2 W is used in order to detect the fine defect located in the vicinity of the surface of the sample W. An outgoing beam diameter is about 1 mm. In order to detect a defect in the sample W, a light source of the type of oscillating visible or infrared laser beams of a wavelength that makes easy for light to penetrate into the sample W is used.

Figure 1B:
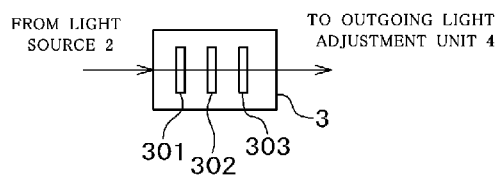
FIG. 1B is a block diagram illustrating one example of a configuration of an attenuator of the defect inspection device according to the first embodiment of the present invention.

As illustrated in FIG. 1B, the attenuator 3 appropriately includes a first polarizing plate 301, a half-wave plate 302 that is rotatable around an optical axis of the illumination light, a second polarizing plate 303 and so forth. The light that has been incident upon the attenuator 3 is converted into linearly polarized light by the first polarzing plate 301, a polarization direction of the light is rotated in an optional direction in accordance with a phase delay axis azimuth angle of the half-wave plate 302, and then the light passes through the second polarizing plate 303. The intensity of light is reduced at an optional rate by controlling the azimuth angle of the half-wave plate 302.

When the degree of linear polarization of the light that is incident upon the attenuator 3 is sufficiently high, the first polarizing plate 301 may not necessarily be demanded. The attenuator 3 of the type that a relation between an input signal and a light-reduction rate is calibrated in advance is used. It is also possible to use an ND filter having a gradation concentration distribution and/or to use a plurality of the ND filters having mutually different concentrations by mutually switching the ND filters as the attenuator 3.

The outgoing light adjustment unit 4 includes a plurality of reflection mirrors 401 and 402. Here, although the embodiment when the outgoing light adjustment unit 4 includes two reflection mirrors will be described, the number of the reflection mirrors is not limited to two and three or snore reflection mirrors may be appropriately used. Here, it is supposed that a three-dimensional rectangular coordinate system (XYZ coordinates) is temporarily defined and incident light upon the reflection mirror is travelling in a +X direction. The first reflection mirror 401 is installed (the light is incident and reflected in an X-Y plane) so as to polarize the incident light in a +Y direction, and the second reflection mirror 402 is installed (the light is incident and reflected in a Y-Z plane) so as to polarize the light that has been reflected from the first reflection mirror 401 in a +Z direction position and a traveling direction (an angle) of the light that goes out of the outgoing light adjustment unit 4 are adjusted by translating the respective reflection mirrors 401 and 402 and adjusting tilt angles of the reflection mirrors 401 and 402.

It becomes possible to perform adjustment of the position and the angle in the X-Z plane and adjustment of the position and the angle in the Y-Z plane of the light (traveling in the +Z direction) that goes out of the outgoing light adjustment unit 4 independently of each other by arranging the first reflection mirror 401 and the second reflection mirror 402 such that the incidence/reflecting surface (the X-Y plane) of the first reflection mirror 401 is orthogonal to the incidence/reflecting surface (the Y-Z plane) of the second reflection mirror 402.

The beam expander 5 includes two or more lens groups and has a function of increasing the diameter of an incident paralleled luminous flux. For example, a Galilean beam expander that includes a combination of a concave lens 501 and a convex lens 502 is used as the beam expander 5. The beam expander 5 is installed on a translation stage of two or more axes and thereby it becomes possible to perform position adjustment such that the center of the beam expander 5 aligns with a predetermined beam position. In addition, the translation stage has a function of adjusting the tilt angle of the entire beam expander 5 such that the optical axis of the beam expander 5 aligns with a predetermined beam optical axis. It is possible to control a rate of magnification of the luminous flux diameter by adjusting a space between the lenses 501 and 502 (a zooming function).

When the light that is incident upon the beam expander 5 is not paralleled, diameter expansion of the luminous flux and collimation (semi-paralleling of the luminous flux) of the luminous flux are simultaneously performed by adjusting the space between the lenses 501 and 502. Collimation of the luminous flux may be also performed by installing a collimate lens on the upstream side of the beam expander 5 independently of the beam expander 5. The rate of magnification of the beam diameter attained by the beam expander 5 ranges from about five times to about ten times and the beam diameter that has been about 1 mm when the beam has been emitted from the light source is increased to a value from about 5 mm to about 10 mm.

The polarization control unit 6 includes a half-wave plate 601, a quarter-wave plate 602 and so forth and controls the polarization state of the illumination light to an optional polarization state. In the middle of the optical path of the illumination unit 101, the optical path is changed by a removable mirror 221 that is freely put into and out of the optical path and the light is made incident upon a beam monitor 22, and thereby the state of the light that is incident upon the beam expander 5 and the state of the light that is incident upon the illumination intensity distribution control unit 7 are measured by the beam monitor 22.

Figure 2A:
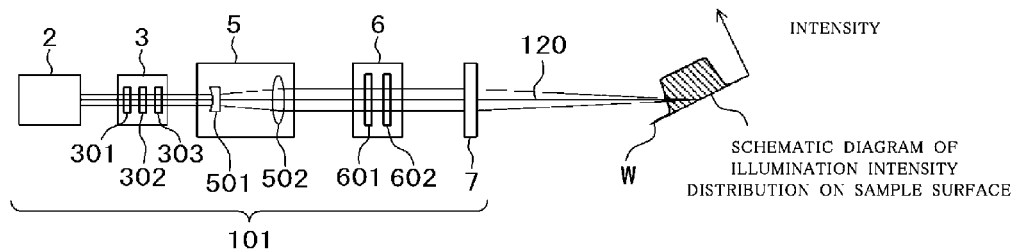
FIG. 2A is a block diagram illustrating one example of an illumination unit and one example of a shape of an illumination intensity distribution on a sample surface to be implemented by the illumination unit of the defect inspection device according to the first embodiment of the present invention.

FIG. 2A to FIG. 5 each is a schematic diagram illustrating one example of a positional relation between an optical axis 120 of the illumination light to be guided from the illumination unit 1091 to the surface of the sample W and an illumination intensity distribution shape. Incidentally, in FIG. 2A to FIG. 5, only some of the constitutional elements of the illumination unit 101 illustrated in FIG. 1A are illustrated and the constitutional elements such as the outgoing light adjustment unit 4, the mirror 21, the beam monitor 22 and so forth are omitted. FIG. 2A is a schematic sectional diagram illustrating one example of an incident surface (a surface including the optical axis of the illumination light and a surface normal of the sample W) in the oblique incidence illumination. The oblique incidence illumination is performed in a state of being inclined relative to the surface of the sample W in the incidence surface. A substantially uniform illumination intensity distribution is created by the illumination unit 101 in the incidence surface. A length of a part where the illumination intensity is uniform ranges from about 100 µm to about 4 mm in order to inspect a wider area in unit time.

Figure 3:
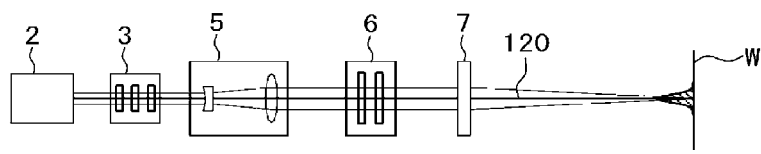
FIG. 3 is a diagram ting one example of a configuration of the illumination unit of the defect inspection device according to the first embodiment of the present invention, that is, a block diagram of the illumination unit that the illumination intensity distribution is in the shape of a Gaussian distribution.
Figure 4:
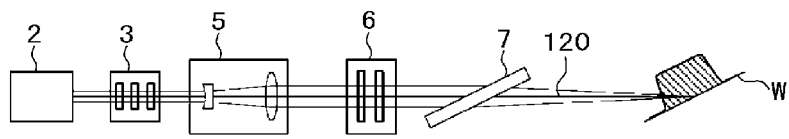
FIG. 4 is a diagram illustrating one example of a configuration of the illumination unit of the defect inspection device according to the first embodiment of the present invention, that is, a block diagram of the illumination unit that the illumination intensity distribution is in the shape of a distribution that is similar to that of a Bessel function of the first kind of order 1 or a sinc function.
Figure 5:
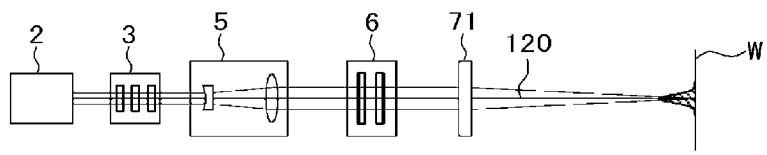
FIG. 5 is a diagram illustrating one example of a configuration of the illumination unit of the defect inspection device according to the first embodiment of the present invention, that is, a block diagram of the illumination unit of the configuration that the diffractive optical element is adopted in an illumination intensity distribution control unit.

FIG. 3 is a schematic sectional diagram illustrating one example of a plane that includes the surface normal of the sample SW and is vertical to the incidence surface of the light for the oblique incidence illumination. In this plane, an illumination intensity distribution that the intensity of the light on a peripheral part is weaker than that on a central part is exhibited on the surface of the sample W. More specifically, a Gaussian distribution that reflects the intensity distribution of the light that is incident upon the illumination intensity distribution control unit 7, or an intensity distribution that reflects an aperture shape of the illumination intensity distribution control unit 7 and is similar to the distribution of a Bessel function of the first kind of order 1 or a sine function as illustrated in FIG. 4 is obtained. A length (a length of a region having an illumination intensity corresponding to at least about 13.5% of a maximum illumination intensity) of the illumination intensity distribution in the plane is shorter than a length of the part where the illumination intensity in the incidence surface is uniform and ranges from about 2.5 µm to about 20 µm in order to reduce the haze generated from the surface of the sample W.

The illumination intensity distribution control unit 7 includes optical elements such as an aspherical lens, a diffractive optical element, a cylindrical lens array, a light pipe and so forth which will be described later. The optical elements which configure the illumination intensity distribution control unit 7 are arranged vertically to the optical axis of the illumination light as illustrated in FIG. 2A and FIG. 3.

Figure 2B:
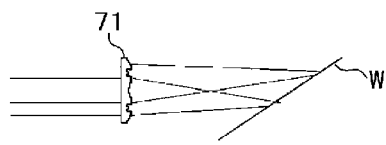
FIG. 2B is a side view illustrating one example of a diffractive optical element of the illumination unit that reduces the shape of the illumination intensity distribution on the sample surface to be implemented by the illumination unit of the defect inspection device according to the first embodiment of the present invention.

The illumination intensity distribution control unit 7 also includes optical elements that act on a phase distribution and an intensity distribution of light that is incident upon the illumination intensity distribution control unit 7. As one of the optical elements included in the illumination intensity distribution control unit 7 a diffractive optical element 71 (DOE, see FIG. 5) is used as illustrated in FIG. 2B. The diffractive optical element 71 is configured by forming a fine uneven shape of a size that is equivalent to or less than the wavelength of the light on a surface of a substrate made of a material that transmits incident light. As the material that transmits the incident light, for example, fused quartz is used for ultraviolet rays. It is preferable to use the diffractive optical element 71 that is coated with an anti-reflection film in order to suppress attenuation of light caused by passing through the diffractive optical element 71. The abovementioned fine uneven shape is formed by using lithography The illumination intensity distribution modeling after the uneven shape of the diffractive optical element 71 is formed on the sample surface by passing the light that has been converted into the semi-paralleled light after having passed through the beam expander through the diffractive optical element 71. The diffractive optical element 71 is designed and fabricated so as to have the uneven shape that is obtained on the basis of a calculation using the Fourier optical theory such that the illumination intensity distribution to be formed on the sample surface exhibits a uniform distribution that is long in an incidence direction and is short in a direction perpendicular to the incidence direction in the incidence surface.

As the optical elements included in the illumination intensity distribution control unit 7, a translation adjustment mechanism (not illustrated) of two or more axes and a rotation adjustment mechanism (not illustrated) of two or more axes are included so as to make it possible to adjust relative position and angle between the illumination intensity distribution control unit 7 and the optical axis of the incident light. Further, a focus adjustment mechanism (not illustrated) that performs focus adjustment by moving in the optical axis direction is included. As alternative optical elements having the same function as the diffractive optical element 71, a combination of the aspherical lens, the cylindrical lens array, and a cylindrical lens, a combination of the light pipe and an imaging lens and so forth may be used.

Figure 1C:
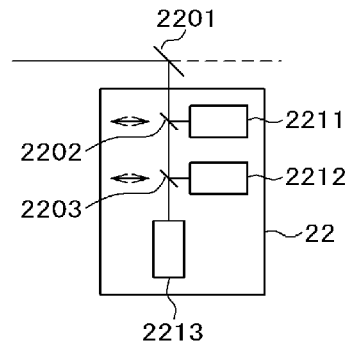
FIG. 1C is a block diagram illustrating one example of a configuration of a beam monitor of the defect inspection device according to the first embodiment of the present invention.

A state of the illumination light in the illumination unit 101 is calculated by a beam monitor 22. The beam monitor 22 includes a position measurement section 2211, an angle measurement section 2212, a wave surface accuracy measurement section 2213 and so forth as illustrated in FIG. 1C and measures and outputs the position and the angle (the traveling direction) of the illumination light that has passed through the outgoing light adjustment unit 4, or the position and the wave surface accuracy of the illumination light that is incident upon the illumination intensity distribution control unit 7.

Measurement of the position of the illumination light is performed by measuring a gravity center position in light intensity of the illumination light. As the specific position measurement section 2211, a position sensitive detector (PSD) and/or image sensors such as a CCD sensor, a CMOS sensor and so forth are used. The illumination light that has been reflected from a mirror 2201 and has been incident upon the beam monitor 22 is reflected from a removable mirror 2202 and is made incident upon the position measurement section 2211, and the gravity center position in light intensity of the illumination light is measured by the position measurement section 2211.

Measurement of the angle of the illumination light is performed by the angle measurement section 2212 that is installed at a position that is more remote from the light source 2 than the position measurement section 2211 or at a condensing position where the light is condensed by a collimate lens. As the specific angle measurement section 2212, a light position sensor, an image sensor or the like is used. The illumination light that has been reflected from the mirror 2201 and has been incident upon the beam monitor 22 is reflected from a removable mirror 2203 and is made incident upon the angle measurement section 2212, and the angle of the illumination light is measured by the angle measurement section 2212.

Information on the position of the condensed illumination light and the angle of the illumination light that have been measured by the position measurement section 2211 and the angle measurement section 2212 is input into the control unit 53 and is displayed on he display unit 54. In a case where the position or the angle of the illumination light shifts from a predetermined position or angle, the position or the angle is adjusted by the outgoing light adjustment unit 4 so as to return to the predetermined position or angle.

Measurement of the wave surface accuracy of the illumination light is performed in order to measure the parallelism of the light to be incident upon the illumination intensity distribution control unit 7. As measurement by the wave surface accuracy measurement section 2213, for example, measurement by a shearing interferometer or measurement by a Shack Hartman wave surface sensor is performed. The illumination light that has been reflected from the mirror 2201 and has been incident upon the beam monitor 22 is incident upon the wave surface accuracy measurement section 2213 in a state of leaving removable mirrors 2202 and 2293 respectively withdrawn from the optical path.

The shearing interferometer is configured such that a sheet of optical glass of about several mm in thickness that the both surfaces have been flatly polished is obliquely inclined and inserted into the optical path of the illumination light and a divergence state and/or a convergence state of the illumination light are/is measured on the basis of a pattern of interference fringes observed when reflected light from a front surface and reflected light from a back surface have been projected onto a screen, and an SPUV-25 manufactured by SIGMA KOKI Co. Ltd. and so forth are available as the shearing interferometer. It is possible to automatically measure the divergence state and/or the convergence state of the illumination light by installing the image sensor such as the CCD sensor, the CMOS sensor and so forth at the position of the screen.

The Shack Hartman wave surface sensor is configured such that the wave surface is projected onto the image sensor such as the CCD sensor and so forth by dividing the wave surface into partial wave surfaces by a fine lens array and an inclination of each partial wave surface is measured from a displacement amount of a projection position. It is possible for the Shack Hartman wave surface sensor to perform detailed wave surface accuracy measurement such as measurement of partial turbulence of the wave surface and so forth in comparison with the shearing interferometer.

In a case where it has been found from the wave surface accuracy measurement that the light to be incident upon the illumination intensity control unit 7 is not the semi-paralleled light and is diverged or converged, it is possible to make the light approximate to the semi-paralleled light by displacing the lens groups 501 and 502 of the front-stage beam expander 5 in an optical axis direction. In addition, in a case where it has been found from the wave surface accuracy measurement that the wave surface of the light to be incident upon the illumination intensity control unit 7 is partially inclined, it is possible to make the wave surface approximate to a flat surface, that is, to make the illumination light approximate to the semi-paralleled light by inserting a spatial light phase modulation element 72 that is one kind of a spatial light modulator (SLM) to the front stage of the illumination intensity control unit 7 and giving an appropriate phase difference to every position of a luminous flux section such that the wave surface becomes flat.

The wave surface accuracy (a deviation from a predetermined wave surface (a designed value or an initial state) of the light that is incident upon the illumination intensity distribution control unit 7 is reduced to not more than about $\lambda/10$ rms by using the abovementioned wave surface accuracy measurement and adjustment sections.

The illumination intensity distribution on the surface of the sample W that has been adjusted by the illumination intensity distribution control unit 7 is measured by the illumination intensity distribution monitor 24 incidentally, as illustrated in FIG. 1A, also when vertical illumination is used, the illumination intensity distribution on the surface of the sample W that has been adjusted by the illumination intensity distribution control unit 7v is measured by an illumination intensity distribution monitor 24v in the same manner. The illumination intensity distribution monitor 24 is configured to form an image of the sample surface on an image sensor 242 such as the CCD sensor, the CMOS sensor and so forth via a lens 241 and detect the illumination intensity distribution on the sample surface as the image.

The image of the illumination intensity distribution that has been detected by the illumination intensity distribution monitor 24 is processed by the control unit 53, a gravity center position of the intensity, a maximum intensity, a maximum intensity position, width and length of the illumination intensity distribution (the width and the length of a region of the illumination intensity distribution that exhibits an intensity that is more than or equal to a predetermined intensity or a ratio that is more than or equal lea predetermined ratio relative to a maximum intensity value) and so forth are calculated and are displayed on the display unit 54 together with a contour shape, a waveform in section and so forth of the illumination intensity distribution.

When the oblique incidence illumination is performed, positional displacement of the illumination intensity distribution and a disturbance in shape of the illumination intensity distribution due to defocusing occur due to elevation displacement of the surface of the sample W. In order to suppress the abovementioned positional displacement and disturbance in shape of the illumination intensity distribution, the elevation of the surface of the sample W is measured, and when the elevation has been displaced, the displacement is corrected by the illumination intensity distribution control unit 7 or by elevation adjustment by the Z axis of the stage 103.

Figure 6:
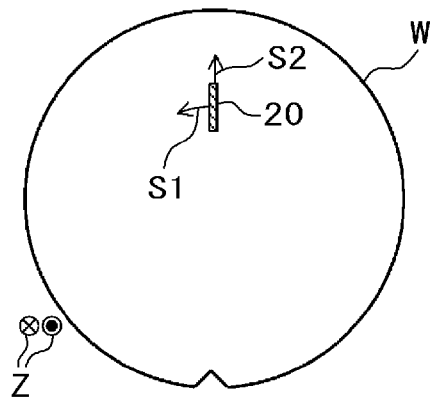
FIG. 6 is a plan view illustrating one example of a sample that exhibits the illumination intensity distribution shape to be implemented by the illumination unit of the defect inspection device according to the first embodiment of the present invention.
Figure 7A:
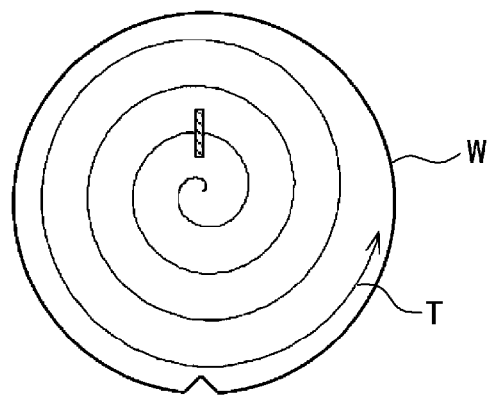
FIG. 7A is a plan view of the sample that exhibits one example of a track of an irradiation region on the sample to be implemented by the illumination unit of the defect inspection device according to the first embodiment of the present invention when illuminating the sample surface spirally by driving a rotation stage.

Examples of a shape (an illumination spot 20) of the illumination intensity distribution formed on the surface of the sample W by the illumination unit 101 and a sample scanning method will be described by using FIG. 6 and FIG. 7A. As the sample W, a circular semiconductor wafer is supposed. The stage 103 includes a translation stage, a rotation stage, a Z-axis stage for sample surface elevation adjustment and so forth (none of them are illustrated). The illumination spot 20 has the illumination intensity distribution that is long in one direction as mentioned above, the abovementioned direction is designated by S2, and a direction that is substantially orthogonal to the direction S2 is designated by S1 (see FIG. 6). The sample is scanned in the direction S1 (in this case, the circumferential scanning direction of the circle centering on an axis of rotation of the rotation stage) by rotational movement of the rotation stage and is scanned in the direction S2 (in this case, the translational scanning direction) of the translation stage by translational movement of the translation stage. While scanning the sample W in the scanning direction S1 one time, the sample W is scanned in the scanning direction S2 by a distance of less than a longitudinal length of the illumination spot 20. Thereby, the illumination spot 20 draws a spiral track T on the sample W and the entire surface of the sample W is scanned as illustrated in FIG. 7A.

Figure 7B:
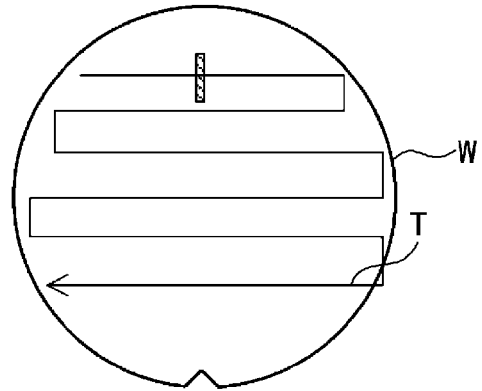
FIG. 7B is a plan view of the sample that exhibits another example of the locus of the irradiation region on the sample to be implemented by the illumination unit of the defect inspection device according to the first embodiment of the present invention when illuminating the sample surface along a straight line by using a two-axis translation stage.

FIG. 7B illustrates one example of scanning of the illumination spot 20 by a configuration that includes a 2-axis translation stage in place of the rotation stage. The sample surface is scanned at a constant speed in a belt-like shape with the illumination spot length in the direction S1 of the illumination spot 20. The translation, stage is moved by a scanning width in the direction S2 at a sample end so as to shift the visual field and then scanning is performed at a constant speed reversely, that is, in the direction S1.

Figure 8:
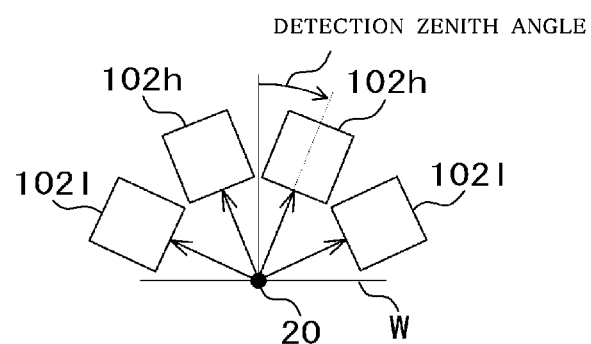
FIG. 8 is a block diagram illustrating one example of a detection unit that includes a plurality of detection units in the defect inspection device according to the first embodiment of the present invention.

FIG. 8 is a side view illustrating one example of arrangement the detection unit 102. An angle of a detection direction (a central direction of a detection aperture) in which the detection unit 102 performs detection relative to the normal line of the sample W is defined as a detection zenith angle. The detection unit 102 appropriately includes a high-angle detection unit 102*h* of not more than about 45 degrees in detection zenith angle, a low-angle detection unit 1021 of at least about 45 degrees in detection zenith angle and so forth. The high-angle detection unit 102*h* and the low-angle detection unit 1021 each includes a plurality of detection units so as to cover the scattered light beams that scatter in many directions at the respective detection zenith angles so set.

Figure 9:
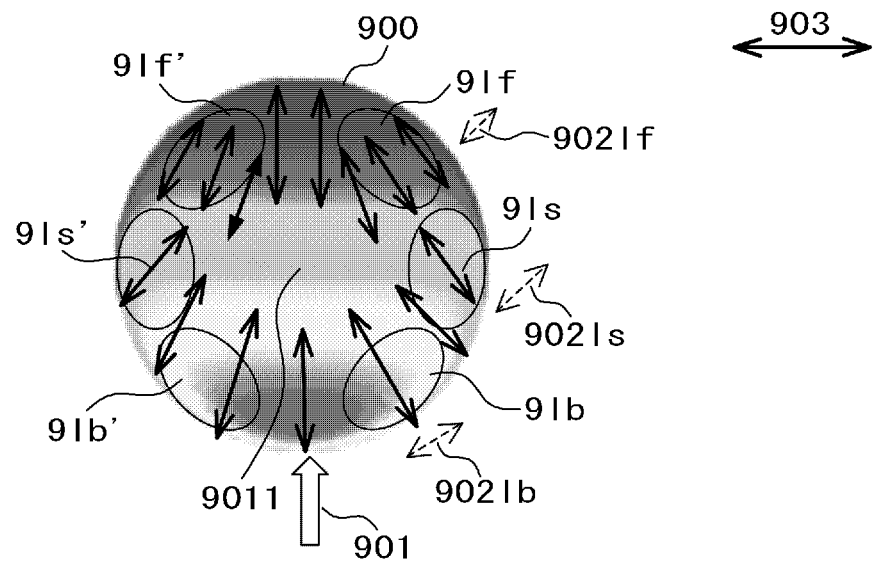
FIG. 9 is a distribution map illustrating one example of a distribution of scattered light at an azimuth angle and a zenith angle that a low-angle detection unit detects in the defect inspection device according to the first embodiment of the present invention.

FIG. 9 illustrates one example of the azimuth angles and the zenith angles that the detection units included in the low-angle detection unit 1021 respectively detect. A detection region of each detection unit is defined three-dimensionally by the zenith angle and the azimuth angle. 900 denotes a distribution of the scattered light when the zenith angle has been set as a radius r and the azimuth angle has been set as an angle θ. An arrow 901 denotes an incidence direction of P-polarized light in oblique illumination. 9011 is an irradiated region on the surface of the sample W that has been irradiated with light by the oblique illumination. An arrow 903 is a polarization direction of the scattered light from the sample W. 91*f*, 91*f'*, 91*s*, 91*s'*, 91*b*, and 91*b'* are regions of the scattered light that the six detection units included in the low-angle detection unit 1021 detect. 91*f* is the region of forward scattered light, 91*b* is the region of backward scattered light, and, in general, the region 91*f* is weaker than the region 91*b* in scattered light intensity. That is, the region 91*f* is more increased than the region 91*b* in contrast to the background scattered light of the defect.

9021*f*, 9021*s*, and 9021*b* respectively denote polarization directions that are orthogonal to polarization of the scattered light from the sample W respectively in the regions 91*f*, 91*s*, and 91*b*.

Figure 10A:
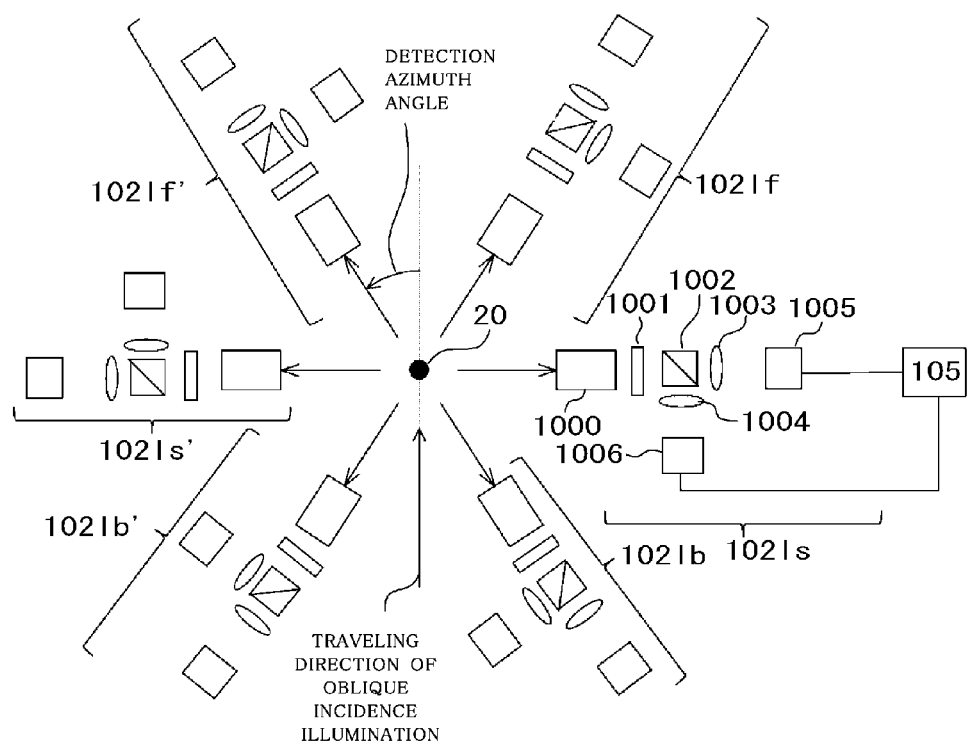
FIG. 10A is a plan view illustrating one example of planar arrangement of the low-angle detection unit in the defect inspection device according to the first embodiment of the present invention.

FIG. 10A illustrates one example of a configuration of the detection unit 1021 that detects the regions 91*f*, 91*f'*, 91*s*, 91*s'*, 91*b*, and 91*b'*. The scattered light generated from the illumination spot 20 is detected by each of detection units 1021*f*, 1021*f'*, 1021*s*, 1021*s'*, 1021*b*, and 1021*b'* included in the low-angle detection unit 1021.

Respective constitutional elements included in the detection unit 1021*s* will be described. The detection unit 1021*s* includes a condensing section 1000, a polarization control section 1001, a polarization beam splitter 1002, lenses 1003 and 1004, light receiving units 1005 and 1006 and so forth. In the abovementioned configuration, after the light has been condensed by the condensing section 1000, the polarization direction of the light is rotated by the polarization control section 1001. As the polarization control section 1001, typically, a half-wave plate that includes a rotationally movable mechanism is used. As the polarization control section 1001, for example, a liquid crystal element, an EO modulator and so forth that make it possible to control the polarization direction by electric control from the outside are also applicable in addition to the abovementioned half-wave plate.

The polarization beam splitter 1002 splits the light into two polarized components that the polarization directions are mutually orthogonal and braches the optical path into two optical paths. The polarized components that have been branched so as to travel along the branched optical paths are respectively condensed by the lenses 1003 and 1004 and are respectively guided to the light receiving units 1005 and 1006 for respectively converting the received light beams into electric signals. The abovementioned configuration is applied to all of the detection units illustrated in FIG. 10A. The electric signal so converted by each light receiving unit is sent to the signal processing unit 105 in FIG. 1 and defect detection processing is performed on the electric signal.

Figure 10B:
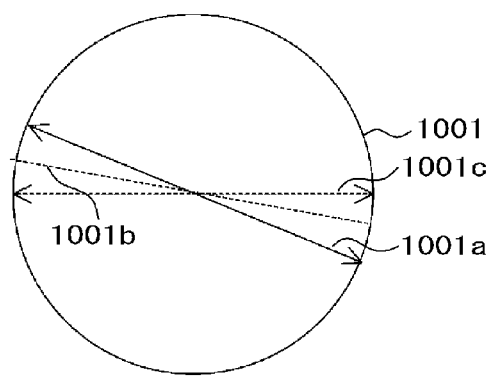
FIG. 10B is a diagram illustrating one example of a rotation angle control method in the defect inspection device according to the first embodiment of the present invention, that is, a diagram illustrating a polarization direction of scattered light from the sample, a phase advance axis of a half-wave plate, and a polarization direction obtained after polarization of the light has been controlled when separating the polarization direction of the light into the polarization direction of the scattered light from the sample and a polarization direction that is orthogonal to the abovementioned polarization direction.

FIG. 10B illustrates one example of a rotation angle control method to be performed by the polarization control section 1001. FIG. 10B illustrates a system adopted when separating the polarization direction of the light into the polarization direction of the scattered light from the sample surface and a polarization direction that is orthogonal to the abovementioned polarization direction. The polarization control section 1001 is configured by a half-wave plate, 1001*a* is the polarization direction of the scattered light from the sample surface, 1001*b* is a phase advance axis of the half-wave plate, and 1001*c* is a polarization direction obtained after polarization of the light in the polarization direction 1001*a* has been controlled. The light directed in the polarization direction 1001*c* is branched by the polarization beam splitter 1002 so as to go toward the optical path that the lens 1003 is arranged. Consequently, the light that is branched by the polarization beam splitter 1002 so as to go toward the side of the optical path that the lens 1003 is arranged is minimized in light amount of the scattered light from the sample surface.

Figure 11A:
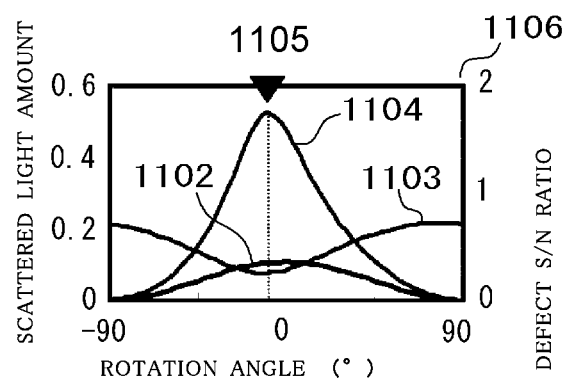
FIG. 11A is a graph indicating one example of a result of simulation of an S/N ratio of a defect signal in the defect inspection device according to the first embodiment of the present invention, that is, the graph indicating an S/N ratio distribution relative to a polarization angle detected by a forward scattered light detection system.
Figure 11B:
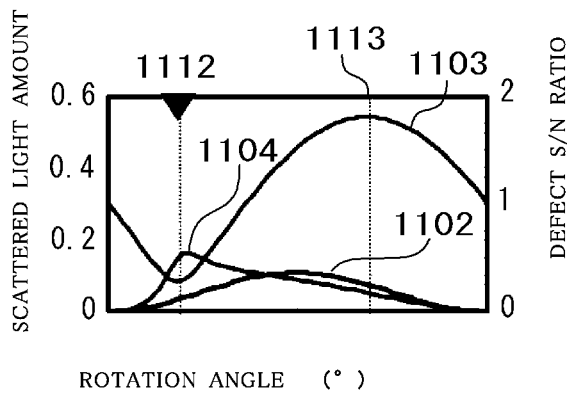
FIG. 11B is a graph indicating another example of the result of simulation of the SN ratio of the defect signal in the defect inspection device according to the first embodiment of the present invention, that is, the graph indicating the S/N ratio distribution relative to a polarization angle detected by a side-way scattered light detection system.

FIG. 11A and FIG. 11B each illustrates one example of a result of simulation of an S/N ratio to be expected when supposing that a spherical defect is present on the sample surface and shot noise that is proportional to 0.5-th power of the amount of the scattered light from the sample surface is generated as noise. FIG. 11A illustrates one example of an S/N ratio distribution of a signal to be detected by the detection unit 1021*f* and FIG. 11B illustrates one example of an S/N ratio distribution of a signal to be detected by the detection unit 1021s. In FIG. 11A and FIG. 11B, the horizontal axis is an angle of polarization at which the polarization direction is rotated by the polarization control section 1001.

In FIG. 11A and FIG. 11B, a curve 1102 indicates an amount of scattered light from the defect of the light that has been branched by the polarization beam splitter 1002 and has travelled to the optical path side that the lens 1004 is arranged, a curve 1103 indicates an intensity of the shot noise generated when detecting the light which has been branched by the polarization beam splitter 1002 and has travel ed to the optical path side that the lens 1004 is arranged by the light receiving unit 1006, and a curve 1104 indicates an expected defect S/N ratio. 1105 in FIG. 11A and 1112 in FIG. 115 each denotes a rotation angle at which the expected defect S/N ratio is maximized.

In the graph indicating the defect S/N ratio of the detection unit 1021f that detects the forward scattered light in. FIG. 11A, at the position 1105 where the rotation angle is almost reduced to zero degrees, the light receiving unit 1006 that detects the light that has been branched by the polarization beam splitter 1002 and has passed through the lens 1004 exhibits a most favorable defect S/N ratio. On the other hand, at that time, the light receiving unit 1005 for the light that travels straight through the polarization beam splitter 1002 exhibits an almost unfavorable defect S/N ratio and merely obtains signals that are very low in defect S/N ratio because defect scattered light (scattered light from the defect) 1106 and the noise are detected.

On the other hand, in the graph that indicates the defect S/N ratio of the detection unit 1021s that detects side-way scattered light in FIG. 11B, at the rotation angle position 1112, although it is possible to obtain the most favorable defect S/N ratio by the light receiving unit 1006 that detects the light that has been branched by the polarization beam splitter 1002 and passed through the lens 1004, the amount of the scattered light from the defect is small on the side of the light receiving unit 1006 and a larger amount of the scattered light from the defect is detected on the optical path side that the light travels straight through the polarization beam splitter 1002 and passes through the lens 1003.

In general, since the state of the surface of the sample W is changed with a fluctuation in manufacturing state, the defect S/N ratio may not necessarily reach the most favorable value at the angles indicated by the graphs in FIG. 11A and FIG. 11B. Accordingly, the signal processing unit 105 may monitor the scattered light from the sample surface, set gains for signals sent from the light receiving units on the two optical paths so branched depending on the polarization, and integrate together the signals.

Specifically, when intensities of the signals of the light receiving units that have been branched depending on polarization are respectively designated by 10 and 11, a band-pass filter that filters these signals is designated by BL, and amounts of scattered light that have been obtained in advance by simulation and expected to be detected by the respective light receiving units are respectively designated by S0 and S1, it is possible to promote improvement of the defect S/N ratio by dynamically setting the gains respectively as "S0/(conv(BL, 10))" and "S1/(conv(BL, 11))" and then performing addition and integration.

As indicated by the graphs in FIG. 11A and FIG. 11B, in the detection unit 1021f for detecting the forward scattered light, even in a case where the optical path is branched into two paths depending on polarization, when the defect S/N ratio of one optical path is optimized, it becomes difficult for the other optical path to obtain a sufficient defect S/N ratio and such a phenomenon occurs that the gain is greatly reduced regardless of calculation by the abovementioned formula. Accordingly, in order to avoid complication of the device and to obtain a sensitivity improving effect, arrangement that is a simplified version of the optical system arrangement in FIG. 10A and is illustrated in FIG. 12 is selected.

Figure 12:
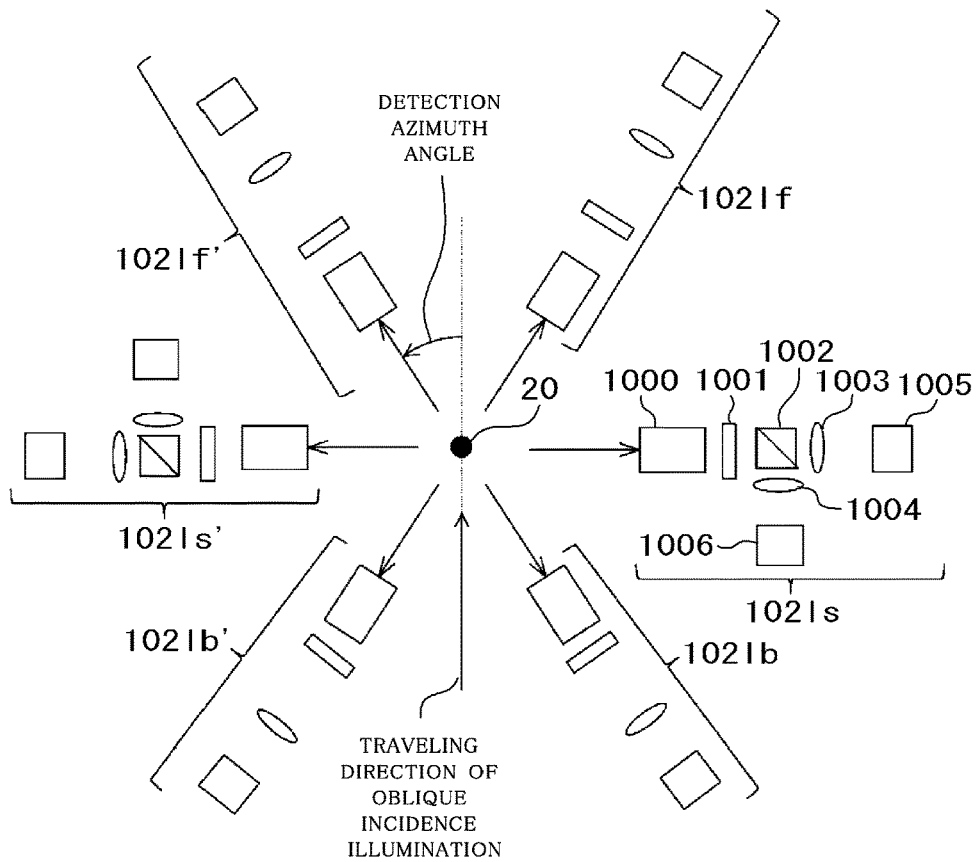
FIG. 12 is a plan view illustrating one example of planar arrangement of the low-angle detection unit when the low-angle detection unit has been configured in a simple manner in the defect inspection device according to the first embodiment of the present invention.

FIG. 12 illustrates one example of an optical system that when performing polarization-based optical path branching, the polarization-based optical path branching is performed only for the detection units 1021s and 1021s' that detect the side-way scattered light that acquisition of many defect scattering signals is expected on the both branched optical paths. The detection unit 1021f for detecting the forward scattered light has a polarization filter that includes a rotationally operable mechanism unit. The polarization filter 1201 that includes the rotationally operable mechanism unit is arranged on each of the detection units 1021f and 1021f' for detecting the forward scattered light on which no optical path branching is performed and the detecting units 1021b and 1021b' for detecting backward scattered light, and the rotation angle is set so as to shield the light in the polarization direction of the scattered light from the sample surface.

Figure 13A:
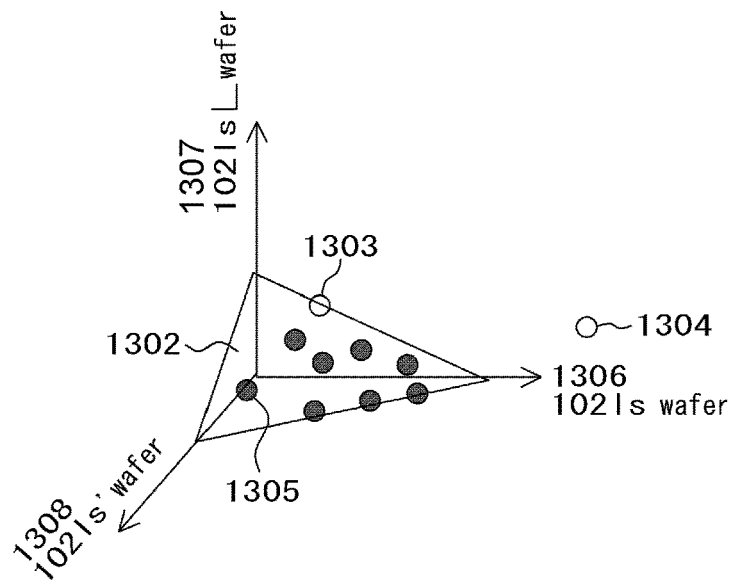
FIG. 13A is a graph indicating one example of a state where a detection signal has been plotted in a multidimensional space in order to describe a defect decision system in the defect inspection device according to the first embodiment of the present invention.

One example of a defect decision system according to the present invention to be executed by the signal processing unit 105 in FIG. 1 is illustrated in FIG. 13A. FIG. 13A is a graph that scattered light beams that have been detected by the respective detection units are converted into the electric signals and signal intensities that have been obtained by performing high-frequency band-pass filtering on the electric signals are plotted in a multi-dimensional space. In respective axes indicative of polarization directions in the multi-dimensional space, polarization directions 1306 and 1307 indicate the signal intensities of the scattered light beams obtained by detecting using the light receiving units 1005 and 1006 of the detection unit 1021s illustrated in FIG. 12. The polarization direction 1306 is a polarization direction expected to match the polarization direction of the scattered light from the sample surface and the polarization direction 1307 is a polarization direction expected to be orthogonal to the polarization direction of the scattered light from the sample surface. In addition, a polarization direction. 1308 of the scattered light is a polarization direction expected to match the polarization direction of the scattered light from the sample surface and indicates a signal intensity detected by the detection unit 1021s'.

In FIG. 13A, a surface 1302 is a surface for discrimination between the noise and the defect, points 1303 and 1304 located at positions more remote from the origin than the discrimination surface 1302 are the defects and a point 1305 located on the origin side is the noise. The point 1304 is the aspherical defect and no sufficient signal is obtained in the polarization direr 1307. Since, in this system, the signal in the polarization direction 1306 and the signal in the polarization direction 1307 are simultaneously used, it is possible to simultaneously detect the defect at the point 1304 and the defect at the point 1303 simultaneous detection of which has been difficult by an existing system.

Since the polarization direction is changed depending on the surface state of a region that the scattered light has been detected on the actual sample surface, it does not mean that the polarization direction of the scattered light from the sample is typically maintained constant during inspection. Accordingly, the distribution of the points 1305 indicative of the noises is changed region by region. In general, the noise is proportional to the 0.5-th power of the scattered light from the sample W.

Figure 13B:
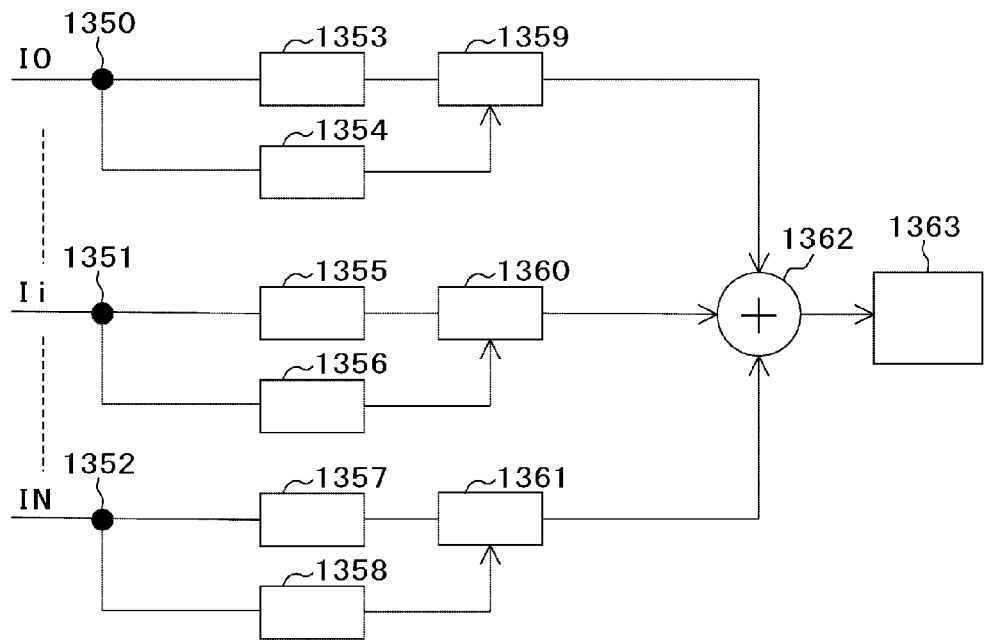
FIG. 13B is a block diagram illustrating one example of a configuration of a unit for executing the defect decision system in the defect inspection device according to the first embodiment of the present invention.

One example of a specific defect decision method to be executed by the signal processing unit 105 is illustrated in FIG. 13B. 1350, 1351, and 1352 respectively denote light amounts l0, li, and lN from the respective detection units. 1353, 1355, and 1357 are high-frequency band-pass filters, 1354, 1356, and 1358 are low-frequency band-pass filters, and 1359, 1360, and 1361 are gains. Here, filter characteristics of the low-frequency band-pass filters 1354, 1356, and 1358 are denoted by BL. The gain is typically set so as to be proportional to "Si/conv(BL, li)". Since, in general, a signal value that is expected as the signal value of the defect is not known individually, a fixed value is set in advance by simulation or from an experiment value as the signal value for the defect. On the other hand, "conv(BL, li)" is an output value of the low-frequency pass-band filters 1354, 1356, and 1358 and changes in real time. 1362 is an adder and 1363 is a decision section. Noise separation on the discrimination surface 1302 illustrated in FIG. 13A is implemented by the abovementioned configuration.

Incidentally, although, here, the method of setting the gain on the basis of the amount of the background scattered light from the sample has been described, it is also possible to adopt other methods of estimating noise amounts by using mutually different systems and setting the gain that is inversely proportional to these noise amounts such as a method of calculating a standard deviation σi of the light amount li in a fixed time and setting a value obtained by normalizing the expected signal value Si with σi as the gain, a method of calculating the standard deviation of by using a fluctuation in luminance of mutually corresponding design regions of different dies, for example, when the sample is a semiconductor wafer and so forth, in addition to the abovementioned method.

According to the present embodiment, it becomes possible to set the gain on the basis of the light amount of the background scattered light from the sample and therefore it becomes possible to obtain the defect signal that is high in S/N ratio by detecting the scattered light from the fine defect on the sample.

First Modification

Figure 14:
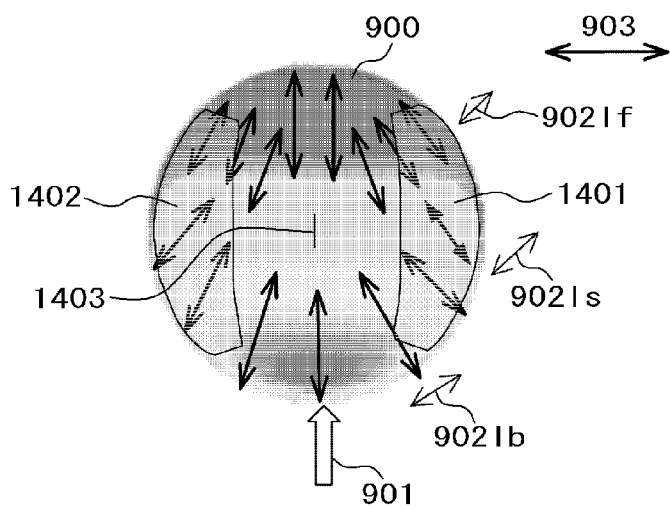
FIG. 14 is a distribution map illustrating one example of a distribution of the scattered light at the azimuth angle and the zenith angle that a low-angle detection unit detects in a defect inspection device according to a first modification of the first embodiment of the present invention.

As the first modification of the first embodiment, one example of a detection unit which is different from the detection unit described in the first embodiment in optical system arrangement will be described. The illumination unit is the same as the illumination unit 101 described in the first embodiment and therefore description thereof is omitted. In the present example, the configuration of the detection unit is different from the configuration of the detection unit 102 described in the first embodiment. FIG. 14 is a diagram illustrating one example of the azimuth angle and the zenith angle of the scattered light from the sample W that the detection unit in the first modification detects. In FIG. 14, the regions and the arrows 900, 901, 9021f, 9021s, 9021b, and 903 are the same as those described in FIG. 9. Regions 1401 and 1402 are regions of the scattered light that the condensing lens captures. 1403 is an illumination region on the surface of the sample W to be illuminated from the direction of the arrow 901. Although, in FIG. 9, the configuration that the scattered light is detected simultaneously by the six detection units has been described, in the configuration illustrated in FIG. 14, detection is performed by two detection units by using a condensing lens that is larger in aperture than the condensing lens used in the first embodiment. In the present example, the illumination intensity distribution control unit 7 is adjusted to set such that the illumination region 1403 is made relatively longer than the illumination region in FIG. 9. The detection units that detect the scattered light from the regions 1401 and 1402 are arranged orthogonally to a longitudinal direction of the illumination region 1403 and make imaging detection possible.

FIG. 15A to FIG. 15D each illustrates each polarization direction at the pupil position of the detection unit for the detection region 1401. In the present example, the detection regions 1401 and 1402 of the detection unit are made relatively large in comparison with the configuration that the detection regions 91f, 91f', 91s, 91s', 91b, and 91b' of the respective detection units are arranged as illustrated in FIG. 9 and therefore it is possible to increase the aperture of the condensing lens. Consequently, at the pupil positon of each condensing lens, polarization directions of the light scattered, from the sample or the defect in the detection regions 1401 and 1402 are different from each other.

Figure 15A:
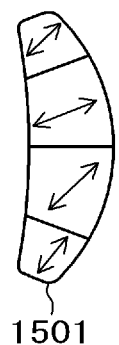
FIG. 15A is a polarization distribution map illustrating one example of a polarization distribution of the scattered light that is incident upon a pupil surface of the low-angle detection unit in.the defect inspection device according to the first modification of the first embodiment of the present invention.
Figure 15B:
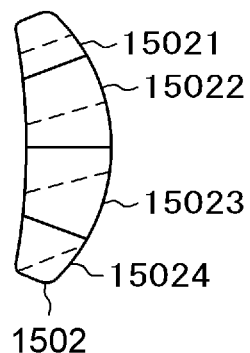
FIG. 15B is a plan view illustrating one example of a polarization state of a half-wave plate that controls polarization of the scattered light that is incident upon the pupil surface of the low-angle detection unit in the defect inspection device according to the first modification of the first embodiment of the present invention.
Figure 15C:
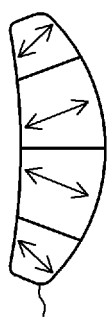
FIG. 15C is a polarization distribution map illustrating one example of a polarization distribution of the light that is scattered from a spherical defect and is incident upon the pupil surface of the low-angle detection unit in the defect inspection device according to the first modification of the first embodiment of the present invention.
Figure 15D:
FIG. 15D is a plan view illustrating one example of a polarization state of the half-wave plate that controls polarization of the light that is scattered from the spherical defect and is incident upon the pupil surface of the low-angle detection unit in the defect inspection device according to the first modification of the first embodiment of the present invention.

FIG. 15A illustrates a polarization direction 1501 at the pupil position of the detection unit for detecting the scattered light in the region 1401 in the scattered light from the sample. FIG. 15B illustrates a half-wave plate 1502 designed so as to have phase advance axes that are made mutually different region by region relative to the polarization direction of the scattered light in the region 1401 in FIG. 15A. The half-wave plate 1502 is divided into four regions 15021 to 15024 and is fabricated so as to have the phase advance axis indicated by a dotted line in each region. By installing the so fabricated half-wave plate 1502 at the pupil position of the detection unit concerned, the polarization directions 1501 of the scattered light from the sample are mutually aligned so as to direct in the same direction after the light has passed through the half-wave plate 1502 installed at the pupil position of the detection unit. FIG. 15C illustrates a polarization direction 1503 of the scattered light from the spherical detect at the pupil position of the detection unit concerned and FIG. 15D illustrates a half-wave plate 1504 that the directions of the phase advance axes are made mutually different region by region, conforming to the polarization directions 1503 at the pupil position of the detection unit concerned. The half-wave plate 1504 is set such that beams of the scattered light from the spherical defect are directed in the same polarization direction at the rear stage.

Figure 16A:
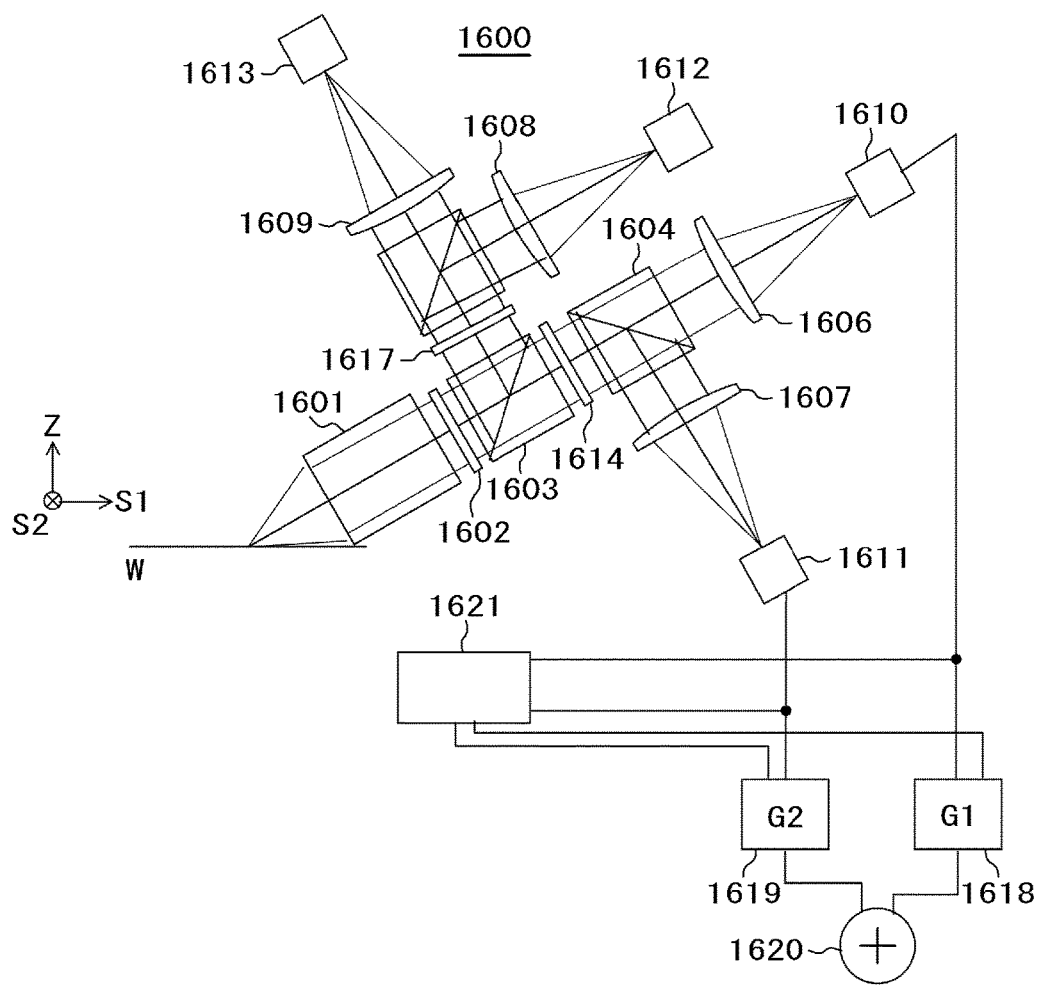
FIG. 16A is a block diagram illustrating one example of a configuration of a detection unit in the defect inspection device according to the first modification of the first embodiment of the present invention.
Figure 16B:
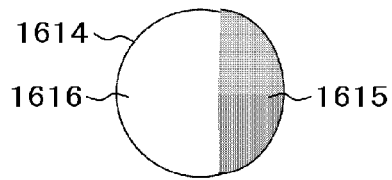
FIG. 16B is a plan view illustrating one example of the half-wave plate used in the detection unit in the defect inspection device according to the first modification of the first embodiment of the present invention.

FIG. 16A is a diagram illustrating one example of optical system arrangement of a detection unit 1600 used for detection of the region 1401 in FIG. 14 in the present example. 1601 is a condensing lens and light that has been condensed by the condensing lens 1601 is guided to a division type half-wave plate 1602. The division type half-wave plate 1602 is configured by using the half-wave plate 1502 illustrated in FIG. 15B or the half-wave plate 1504 illustrated in FIG. 15D. As arrangement of the division type half-wave plate 1602, the plurality of half wave plates 1602 of mutually different designs are prepared so as to allow switching from one half-way plate to another half-way plate by an unillustrated control mechanism. 1603 is a polarization beam splitter that branches the optical path into two optical paths in accordance with a difference in polarization. 1617 and 1614 are half-wave plates that the phase advance axes are made mutually different region by region in order to further branch the optical path into partial optical paths. The configuration of the half-wave plate 1614 is illustrated in FIG. 16B.

The half-wave plate 1614 is divided into two regions 1615 and 1616 and the phase advance exes of the regions 1615 and 1616 mutually deviate by about 45 degrees. In general, the half-wave plate 1614 is divided into the two regions 1615 and 1616 in an S2 axis direction in FIG. 16A so as to make it possible to divide the scattered light into forward scattered light and backward scattered light. In the present example, the phase advance axes of the regions 1615 and 1616 are set such that the total amount of light that has passed through the region 1615 penetrates into an optical path that a lens 1606 is arranged in a rear-stage polarization beam splitter 1604 and the total light that passes through the region 1616 travels toward an optical path that a lens 1607 is arranged.

1610 and 1611 are imaging type line sensors that each detects light amounts of a plurality of spatially separated pixels in a lump. Typically, APD one-dimensional arrays, one-dimensional CCD sensors and so forth are used as the imaging type line sensors 1610 and 1611. The lens 1606 makes the sensor 1610 form an image of the sample surface. The lens 1607 makes the sensor 1611 form the image of the sample surface. The sensors 1610 and 1611 respectively include unillustrated position control mechanisms so as to make it possible to adjust such that the respective pixels arranged in the sensors are mutually aligned among the plurality of sensors 1601 and 1611.

1618 and 1619 are signal conversion units that are configured to respectively multiply signals obtained by the sensors 1610 and 1611 by desired gains G1 and G2. 1620 is an addition unit that is configured to perform addition for every mutually corresponding pixels in the signal conversion units 1618 and 1619. 1621 is a gain setting unit 1621 that is configured to perform time-direction low-frequency filtering pixel by pixel and to set the gains G1 and G2 of the signal conversion units 1618 and 1619 on the basis of a light amount that has been detected after filtered. Typically, the gain setting unit 1621 imparts the gains that are inversely proportional to the magnitude of the detected light amount to the signal conversion units 1618 and 1619.

1617 is a half-wave plate 1617 that is divided into two regions that are almost the same as the regions of the half-wave plate 1614. The light the polarization direction of which has been changed by the half-wave plate 1617 is subjected to optical path branching by a rear-stage polarization beam splitter, and the branched light beams respectively form images of the sample surface on imaging type linear sensors 1612 and 1613 through lenses 1608 and 1609. The imaging type linear sensors 1612 and 1613 respectively convert the detected light beams into electric signals via unillustrated gain setting units, signal conversion units, and addition units and make a defect decision on the basis of the electric signals in combination with a result of calculation by the addition unit 1620.

According to the configuration illustrated in FIG. 16A, the pupil is branched into two parts, and light beams that passes through the branched two pupil parts are respectively detected by the sensors and added together by multiplying the light beams respectively by the gains Thereby, it becomes possible to increase the S/N ratio of a signal that is obtained by integrating together the light beams by setting the high gain one light beam that passes through the pupil part that the high S/N ratio is expected and the low gain to another light beam.

Figure 17A:
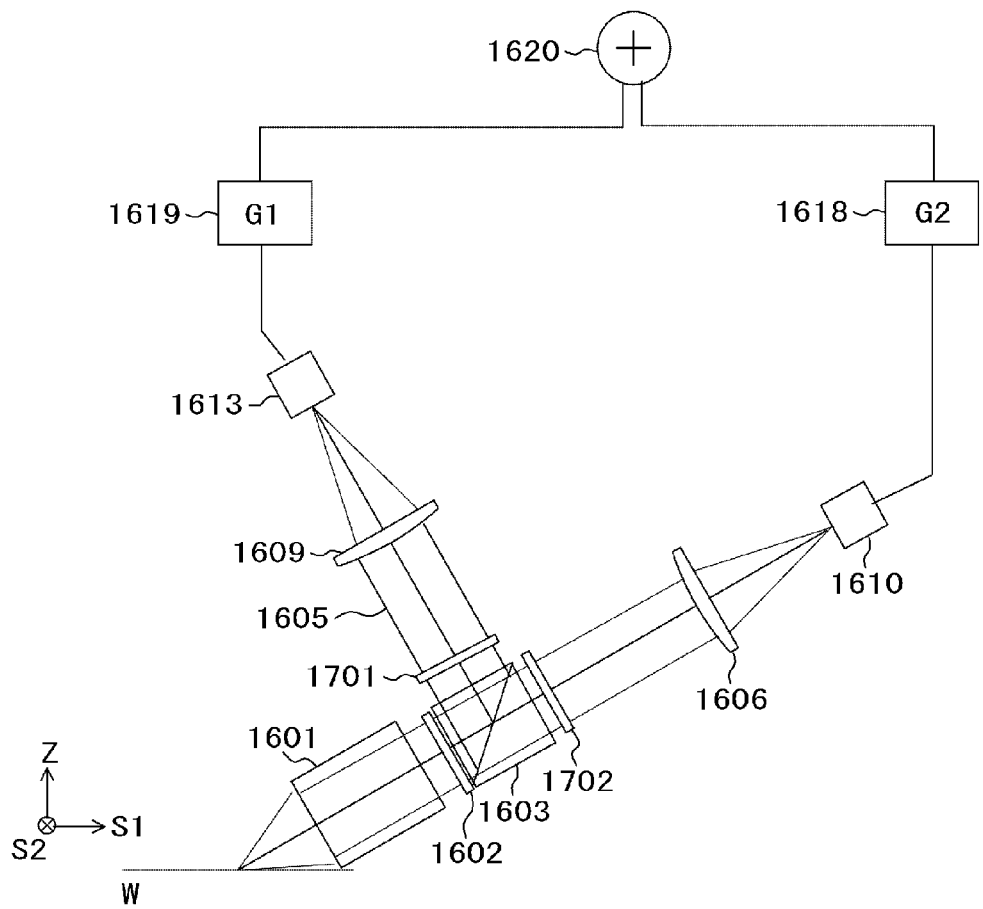
FIG. 17A is a block diagram illustrating one example of a simplified configuration version of the detection unit in the defect inspection device according to the first modification of the first embodiment of the present invention.
Figure 17B:
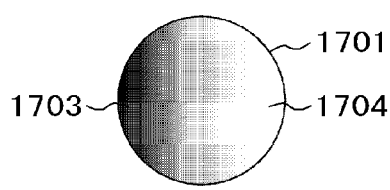
FIG. 17B is a plan view illustrating one example of an aperture used in the simplified configuration version of the detection unit in the defect inspection device according to the first modification of the first embodiment of the present invention.

FIG. 17A illustrates one example of a simplified configuration version of the detection unit 1600 illustrated in FIG. 16A and FIG. 16B. In the configuration illustrated in FIG. 16A and FIG. 16B, the polarization beam splitters 1604 and 1605 for further branching the optical path are installed at the rear stages of the polarization bean splitter 1603 so as to perform pupil division. On the other hand, in the configuration illustrated in FIG. 17A, the pupil division is not performed and apertures 1701 and 1702 are installed. As in en example of the aperture 1701 illustrated in FIG. 17B, as each of the apertures 1701 and 1702, an ND filter that transmittances are made mutually different region by region is used and, typically, the transmittance of the forward scattered light is set high.

According to the present modification, the scattered light from the fine detect on the sample is detected and thereby it becomes possible to obtain the defect signal that is high in S/N ratio.

Second Modification

Figure 18:
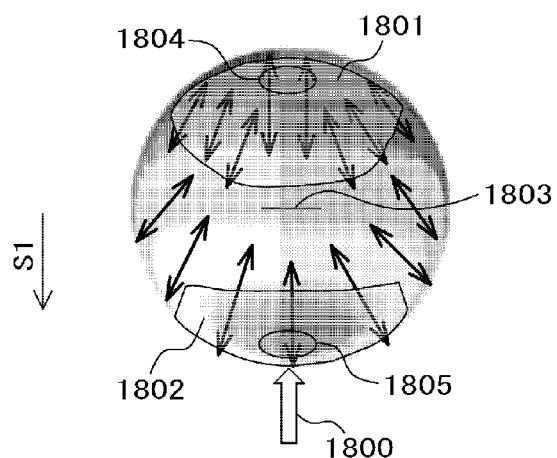
FIG. 18 is a distribution map illustrating one example of a distribution of the scattered light at the azimuth angle and the zenith angle that a low-angle detection unit detects in a defect inspection device according to a second modification of the first embodiment of the present invention.

FIG. 18 is an explanatory diagram illustrating one example of scattered light to be captured by lenses when the optical system has been arranged differently from the optical systems of the first embodiment and the first modification as the second modification of the first embodiment. The illumination unit is the same as the illumination unit 101 described in the first embodiment and therefore description thereof is omitted. In the present modification, setting has been made such that the illumination region 1403 of the sample W to be irradiated with oblique illumination light is made relatively longer than the illumination region 1403 in FIG. 9 by adjusting the illumination intensity distribution control unit 7. The configuration of the detection unit 1600 in the present modification is basically the same as the configuration of the detection unit described in the first modification by using FIG. 16A and therefore description thereof is omitted.

In FIG. 18, an arrow 1800 indicates a direction of illumination with laser. 1801 and 1802 denote capturing ranges of scattered light to be respectively detected by lenses. 1803 is an illumination pattern on the sample surface. The longitudinal direction of this illumination pattern is shifted from the longitudinal direction of the illumination pattern 1403 described in the first modification using FIG. 14 by about 90 degrees. It is possible to implement 90-degree shifting of the orientation of the longitudinal direction by replacing the diffractive optical element 71 of the illumination intensity distribution control unit 7 with an element (not illustrated) suited to shift the orientation of the longitudinal direction by about 90 degrees. The sample is scanned in the direction S1 that is orthogonal to the longitudinal direction of the illumination pattern 1803.

A region 1804 is a region for removing directly reflected light and, typically, a mirror (not illustrated) is installed at a rear stage to exclude the directly reflected light from the optical path. A region 1805 is a range that is used to pass the illumination light and therefore is not used as the detection region.

Figure 19:
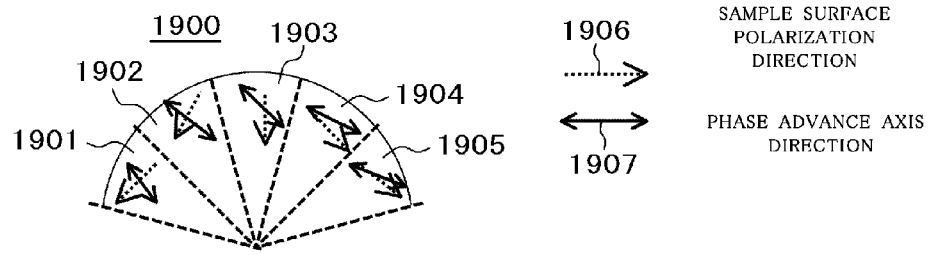
FIG. 19 is a plan view illustrating one example of one configuration of a five-divided polarizing plate used in the low-angle detection in the defect inspection device according to the second modification of the first embodiment of the present invention.

FIG. 19 is an explanatory diagram illustrating one example of a five-divided half-wave plate 1900 to be put into the pupil of the detection unit that detects the region 1804 in the scattered light capturing range 1801 to he detected by the lens. 1901 to 1905 respectively denote divided regions of the half-wave plate 1900, the polarization direction of the scattered light from the sample surface is indicated by a dotted-line arrow 1906, and the phase advance axis of each region of the half-wave plate 1900 is indicated by a solid-line arrow 1907. There is used the half-wave plate 1900 that has been divided into the five regions such that the polarization directions of the scattered light from the sample surface are mutually aligned by adjusting the advance phase axes of the half-wave plate region by region. Thereby, the optical path is branched into the optical path that allows passage of the scattered light from the sample surface and the optical path that does not allow passage of the scattered light by a polarization beam splitter that is installed at the rear stage and thereby it becomes possible to obtain the S/N ratio of the defect that is high, in particular, in contrast on the optical path that does not allow passage of the scattered light.

Figure 20:
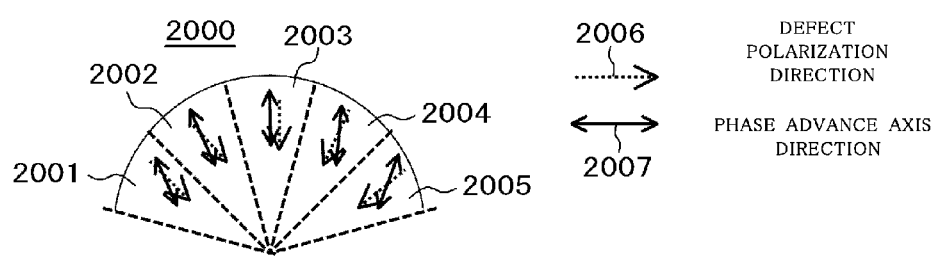
FIG. 20 is a plan view illustrating one example of another configuration of the five-divided polarizing plate used in the low-angle detection in the defect inspection device according to the second modification of the first embodiment of the present invention.

FIG. 20 is also an explanatory diagram illustrating one example of a division type half-wave plate 2000 that is designed differently from the half-wave plate 1900 in FIGS. 19. 2001 to 2005 respectively denotes divided regions of the division type half-wave plate 2000, dotted-line arrow 2006 indicates the polarization direction of the scattered light from the defect and a solid-line arrow 2007 indicates the phase advance axis of each region for making the polarization direction of the scattered light from the defect linear. Owing to provision of the division type half-wave plate 2000, it becomes possible to guide total scattered light from the defect to one optical path after branched by the rear-stage polarization beam splitter.

According to the present modification, the scattered light from the fine defect on the sample is detected and thereby becomes to obtain the defect signal that is high in S/N ratio.

Second Embodiment

Figure 21:
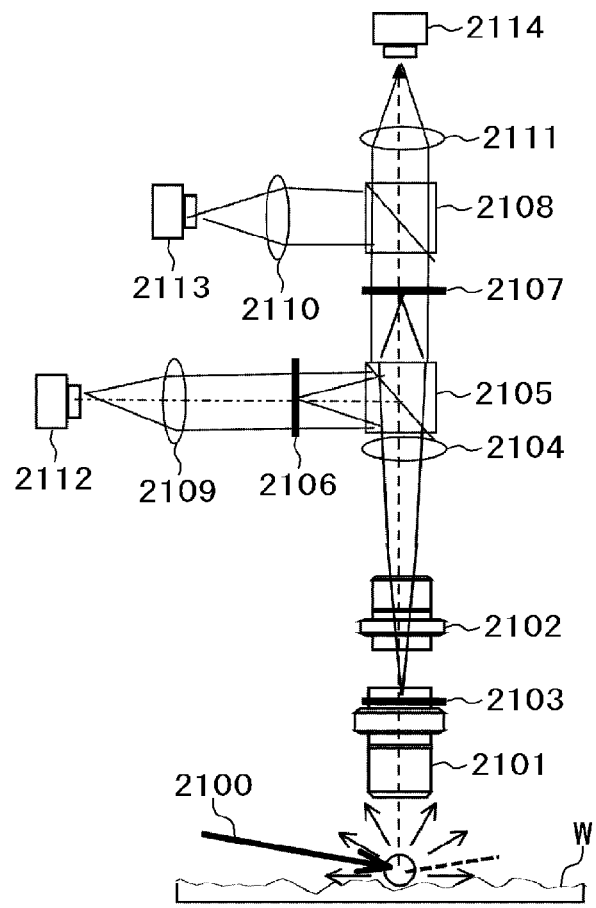
FIG. 21 is a block diagram illustrating one example of a configuration of a detection unit in a defect inspection device according to a second embodiment of the present invention.

The second Embodiment of the present invention will be described by using drawings. FIG. 21 is a diagram illustrating one example of a configuration of a defect inspection device with one detection unit being installed directly on the defect inspection device according to the second embodiment. An illumination unit in the present embodiment is of the type that in the illumination unit 101 described in the first embodiment using FIG. 1A, the system for illuminating the sample from a vertical direction via the illumination intensity distribution control unit 7v is not included and an optical system that obliquely illuminates the sample W with illumination light 2100 via the illumination intensity distribution control unit 7 is included. The configuration of the optical system for obliquely illuminating the sample W with the illumination light 2100 via the illumination intensity distribution control unit 7 is the same as the configuration described in the first embodiment and therefore description thereof is omitted.

In the configuration illustrated in. FIG. 21, the light from the sample surface that is obtained by illuminating the surface of the sample W with the p-polarized oblique illumination light 2100 from an unillustrated illumination unit is captured by an objective lens 2101. 2103 is a division type half-wave plate and the detailed structure of the division type half-wave plate 2103 will be described later. 2102 and 2104 are relay lenses. 2105 is a polarization beam splitter that branches the optical path into two optical paths. 2106 is a movable space filter that typically shields the rearward scattered light. 2107 is a division type half-wave plate 2107 that is used to further branch the optical path into two optical paths by a polarization beam splitter 2108. 2109, 2110, and 2111 are imaging lenses that respectively form images on sensor surfaces of sensors 2112, 2113, and 2114 that are respectively installed at the rear stages of the lenses 2109, 2110, and 2111. As the sensor, typically, a two-dimensional CCD, a TDI liner sensor and so forth are used.

Figure 22:
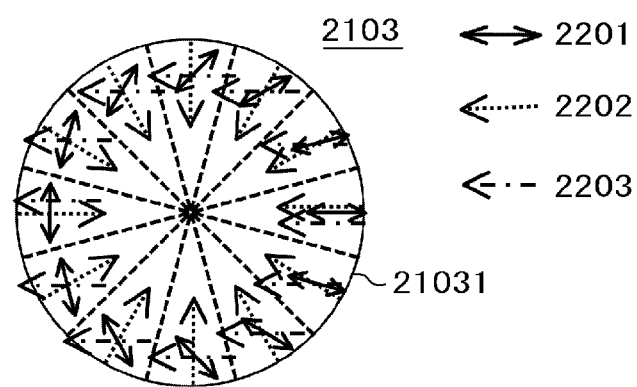
FIG. 22 is a plan view illustrating one example of one configuration of a half-wave plate used in the detection unit in the defect inspection device according to the second embodiment of the present invention.

FIG. 22 is a diagram illustrating one example of a configuration of the division type half-wave plate 2103. The division type half-wave plate 2103 is configured by combining together a plurality of concentrically divided half-wave plates 21031 and a solid-line arrow 2201 indicates each phase advance axis. A dotted-line arrow 2202 indicates each polarization direction of scattered light from a granular defect. The polarization direction indicated by the dotted-line arrow 2202 is changed to a polarization direction indicated by a one-dot chain line arrow 2203 in accordance with the direction of the phase advance axis indicated by the solid-line arrow 2201. Thereby, it becomes possible to separate one optical path into an optical path that the scattered light from the granular defect is thoroughly captured and other optical paths by the rear-stage polarization beam splitter 2105. However, in case of a non-granular defect, the polarization direction is different from the polarization direction of the scattered light from the granular defect, and therefore it does not mean that the scattered light from all kinds of defects is thoroughly captured on one optical path.

Figure 23:
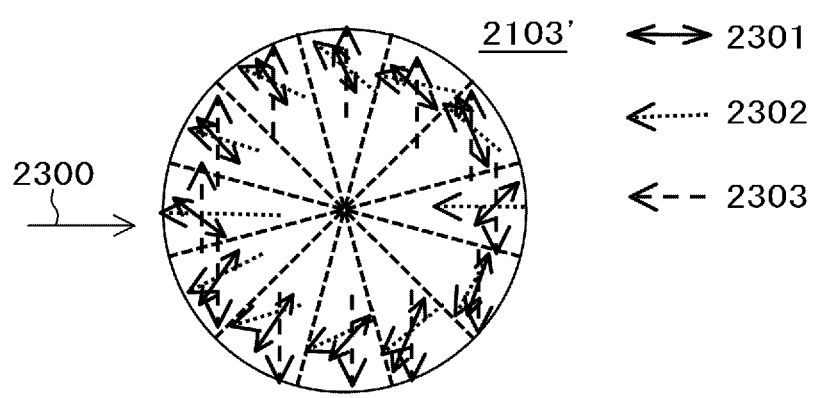
FIG. 23 is a plan view illustrating one example of another configuration of the half-wave plate used in the detection unit in the defect inspection device according to the second embodiment of the present invention.

FIG. 23 illustrates one example of a configuration of a division type half-wave plate 2103' that is different in configuration from the division type half-wave plate 2103 in FIG. 22. A solid-line arrow 2301 indicates each direction of the phase advance axis of each divided half-wave plate, and a polarization direction 2302 of the scattered light from the surface of the sample W that has been irradiated with oblique illumination 2300 from an unillustrated illumination unit is changed to a polarization direction 2303 in accordance with the direction of the phase advance axis. The direction of the phase advance axis is set such that not only switching of the optical path by the polarization beam splitters 2105 and 2108 is performed, but also a phase shift of the phase of the scattered light from the defect is minimized region by region, in particular, after the light has passed through the division type half-wave plate 2103'. On the other hand, the scattered light from the surface of the sample W has a tendency that a bright-spot-like interference disappears on an imaging surface (the sensor surface of each of the sensors 2112, 2113, and 2114) with a phase shift of about 180 degrees. Therefore, the direction of the phase advance axis is also set such that it becomes difficult for the scattered light beams from the surface of the sample W to come into an in-phase state.

Figure 24:
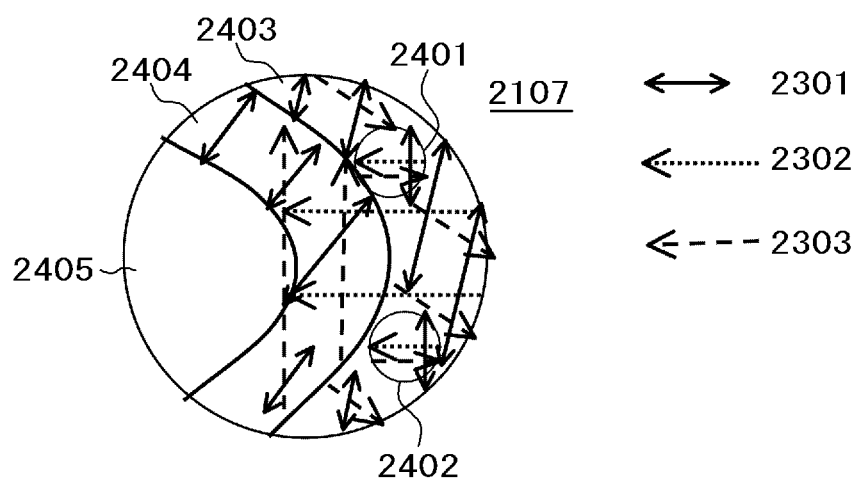
FIG. 24 is a plan view illustrating one example of a configuration of a division type wavelength plate used in the detection unit in the defect inspection device according to the second embodiment of the present invention.

FIG. 24 illustrates one practical example of a configuration of the division type half-wave plate 2107. Here, the setting is the same as that when the division type half-wave plate 2103 has been arranged at the rear stage of the objective lens 2101 as rated in FIG. 21. The division type half-wave plate 2107 is divided into regions 2403, 2404, and 2405. In the abovementioned regions, each of the regions 2403 and 2404 is configured by a half-wave plate.

Regions 2401 and 2402 of the half-wave plate 2403 of the division type half-wave plate 2107 are regions in each of which a high S/N ratio signal is obtained for the granular defect because the polarization direction of the scattered light from the granular defect is orthogonal to the polarization direction of the scattered light from the surface of the sample W. The solid-line arrow 2301 indicates the phase advance axis of each of the half-wave plates 2403 and 2404, and the dotted-line arrow 2302 indicates the polarization direction of the light guided to each of the half-wave plates 2403 and 2404. The polarization directions of the scattered light in the regions 2401 and 2402 are out of phase with the phase advance axis of the half-wave plate 2403 by about 180 degrees and the light thoroughly passes through the rear-stage polarization beam splitter 2108 and is guided to the sensor 2114.

On the other hand, the light that has passed through regions other than the regions 2401 and 2402 of the half-wave plate 2403 is branched by the polarization beam splitter 2108 and the light so branched is detected by both of the sensors 2114 and 2113. The light that has passed through the region of the half-wave plate 2404 is rotated in polarization direction by about 90 degrees relative to the light that has passed through the region. 2401 or 2402 of the half-wave plate 2403, and the light that has passed through the region of the half-wave plate 2404 is thoroughly reflected by the polarization beam splitter 2108 and is guided to the sensor 2113. The region 2405 is a light-shielded region. The intensity of the the scattered light from the sample surface is too strong and therefore the region 2405 light-shielded as a region that the contrast of the defect is insufficient.

Images that have been respectively obtained by the sensors 2112, 2113, and 2114 are added and integrated together by using mechanisms such as, for example, the gain mechanisms (the signal conversion units) 1618 and 1619, the addition unit 1620 and so forth illustrated in FIG, 16A. In addition, as an integration method to be adopted, it is also possible to discriminate between the defect and the noise, for example, by fetching all of not-yet-integrated images into an arithmetic operation unit and by using a known decision technique and a discriminator such as, for example, a support vector machine and so forth, in the feature amount space illustrated in FIG. 13A, not limited to the above mentioned method.

According to the abovementioned embodiments, the scattered light from the fine defect on the sample is detected using the signals that have been detected by the upper detection system and thereby it becomes possible to obtain the high S/N ratio defect signal.

What is claimed is:

1. A defect inspection method, comprising:
   adjusting a polarization state and an intensity distribution of laser that has been emitted from a light source unit, shaping the laser into light that is long in one direction and is short in a direction that is orthogonal to the one direction, and irradiating a surface of a sample with the shaped laser light from a direction inclined relative to a normal direction of the surface of the sample;
   condensing scattered light beams generated from the sample that has been irradiated with the shaped laser light and detecting the condensed light beams by a plurality of detectors;
   processing signals obtained by detecting the scattered light beams by the plurality of detectors and extracting a defect on the surface of the sample; and
   outputting information on the extracted defect,
   wherein condensing the scattered light beams and detecting the condensed light beams by the plurality of detectors are performed by:
   (a1) condensing the scattered light beams generated from the sample that has been irradiated with the laser by a condensing lens,
   (a2) adjusting a polarization direction of the scattered light beams that have been condensed by the condensing lens,
   (a3) mutually separating the scattered light beams of which the polarization directions have been adjusted depending on the polarization direction, and
   (a4) detecting the respective scattered light beams that have been mutually separated depending on the polarization direction,
   wherein detecting the scattered light beams is performed by:
   (b1) detecting the scattered light beams in a plurality of mutually different azimuth angle directions relative to an irradiation direction of the laser with which the surface of the sample is irradiated,
   wherein processing the signals obtained by detecting the scattered light beams by the plurality of detectors and extracting the defect on the surface of the sample are performed by:
   (c1) processing output signals that have been adjusted by respectively multiplying detection signals of the respective scattered light beams so separated depending on the polarization direction by gains and have been output from the plurality of detectors that have detected the scattered light beams, discriminating between a noise and a defect, and
   (c2) detecting the defect.

2. The defect inspection method according to claim 1, wherein adjusting the polarization directions of the scattered light beams that have been condensed by the condensing lens is performed by adjusting the polarization directions by using a wavelength plate of which directions of phase advance axes are made mutually different region by region.

3. The defect inspection method according to claim 1, wherein detecting the scattered light beams is performed by detecting light that has been scattered in the direction that is orthogonal to the one direction respectively on both sides of the direction that is orthogonal to the one direction, relative to a region on the sample to be irradiated with the laser that has been shaped long in the one direction and short in the direction that is orthogonal to the one direction.

4. The defect inspection method according to claim 1, wherein a signal amount of detection signals of the mutually separated scattered light beams or a fluctuation in detection signal of the scattered light beams is calculated and the gains are determined on the basis of the calculated signal amount or fluctuation in detection signal.

5. The defect inspection method according to claim 4, wherein detecting the scattered light beams is performed by detecting the scattered light beams in a plurality of mutually different azimuth angle directions relative to an irradiation direction of the laser with which the surface of the sample is irradiated.

6. The defect inspection method according to claim 4, wherein adjusting the polarization directions of the scattered light beams that have been condensed by the condensing lens is performed by adjusting the polarization directions by using a wavelength plate of which directions of phase advance axes are made mutually different region by region.

7. The defect inspection method according to claim 4, wherein detecting the scattered light beams is performed by detecting light that has been scattered in the direction that is orthogonal to the one direction respectively on both sides of the direction that is orthogonal to the one direction, relative to a region on the sample to be irradiated with the laser that has been shaped long in the one direction and short in the direction that is orthogonal to the one direction.

8. A defect inspection device, comprising:
   a light source unit that emits laser;
   a laser irradiation unit that adjusts a polarization state and an intensity distribution of the laser that has been emitted from the light source unit, shapes the laser into light that is long in one direction and is short in a direction that is orthogonal to the one direction, and irradiates a surface of a sample with the shaped laser light from a direction inclined relative to a normal direction of the surface of the sample;
   a scattered light detection unit that condenses and detects scattered light beams generated from the sample that has been irradiated with the laser by the laser irradiation unit;

a processor that processes signals obtained by detecting the scattered light beams by a plurality of detectors of the scattered light detection unit and extracts a defect on the surfaces of the sample; and a display that outputs information on the defect that has been extracted by the processor, wherein the scattered light detection unit includes:

(A1) a condensing lens that condenses the scattered light beams generated from the sample that has been irradiated with the laser, a polarization light reflector that adjusts polarization directions of the scattered light beams condensed by the condensing lens, (A2) a polarization separation unit that mutually separates the scattered light beams of which the polarization directions have been adjusted by the polarization light reflector depending on the polarization direction, and (A3) a plurality of detectors that detect the respective scattered light beams that have been separated depending on the polarization direction by the polarization separation unit, wherein a plurality of the scattered light detection units are arranged in mutually different azimuth angle directions relative to an irradiation direction of the laser with which the surface of the sample is irradiated by the laser irradiation unit, wherein the processor includes:

(C1) a gain setting unit that sets gains for output signals from the plurality of detectors of the scattered light detection unit that have detected the scattered light beams, and (C2) a defect decision unit that processes the output signals that have been adjusted by the gains set by the gain setting unit and have been output from the plurality of detectors, discriminates between a noise and defect, and detects the defect.

9. The defect inspection device according to claim 8, wherein the polarization light reflector includes a wavelength plate of which directions of phase advance axes are made mutually different region by region, and adjusts the polarization directions of the scattered light beams that have been condensed by the condensing lens by using the wavelength plate.

10. The defect inspection device according to claim 8, wherein one pair of the scattered light detection units is facingly arranged in the direction that is orthogonal to the one direction, relative to a region on the sample to be irradiated with the laser that has been shaped long in the one direction and short in the direction that is orthogonal to the one direction by the laser irradiation unit.

11. The defect inspection device according to claim 8, wherein the gain setting unit calculates a signal amount of detection signals of the plurality of detectors of the scattered light detection unit that have detected the scattered light beams so separated by the polarization separation unit or a fluctuation in detection signal of the scattered light beams of the plurality of detectors, and determines the gain on the basis of the calculated signal amount or fluctuation in detection signal.

12. The defect inspection device according to claim 11, wherein a plurality of the scattered light detection units are arranged in mutually different azimuth angle directions relative to an irradiation direction of the laser with which the surface of the sample is irradiated by the laser irradiation unit.

13. The defect inspection device according to claim 11, wherein the polarization light reflector includes a wavelength plate that directions of phase advance axes are made mutually different region by region, and adjusts the polarization directions of the scattered light beams that have been condensed by the condensing lens by using the wavelength plate.

14. The defect inspection device according to claim 11, wherein one pair of the scattered light detection units is facingly arranged in the direction that is orthogonal to the one direction, relative to a region on the sample to be irradiated with the laser that has been shaped long in the one direction and short in the direction that is orthogonal to the one direction by the laser irradiation unit.

* * * * *